(12) United States Patent
Taylor et al.

(10) Patent No.: US 6,304,773 B1
(45) Date of Patent: Oct. 16, 2001

(54) AUTOMATIC DETECTION AND REPORTING OF CARDIAC ASYSTOLE

(75) Inventors: James W. Taylor, Seattle; Ronald E. Stickney, Edmonds, both of WA (US)

(73) Assignee: Medtronic Physio-Control Manufacturing Corp., Redmond, WA (US)

( * ) Notice: Subject to any disclaimer, the term of this patent is extended or adjusted under 35 U.S.C. 154(b) by 0 days.

(21) Appl. No.: 09/316,468

(22) Filed: May 21, 1999

Related U.S. Application Data

(60) Provisional application No. 60/086,564, filed on May 21, 1998.

(51) Int. Cl.$^7$ .................................................. A61B 5/046
(52) U.S. Cl. ............................... 600/515; 600/518; 607/5
(58) Field of Search .................................... 600/515–518; 607/5; 128/920, 923, 925

(56) References Cited

U.S. PATENT DOCUMENTS

| | | |
|---|---|---|
| 4,523,595 | 6/1985 | Zibell . |
| 4,531,527 | * 7/1985 | Reinhold, Jr. et al. ............. 600/509 |
| 4,610,254 | 9/1986 | Morgan et al. . |

(List continued on next page.)

FOREIGN PATENT DOCUMENTS

| | | |
|---|---|---|
| 0424665A2 | 5/1991 | (EP) . |
| 0469817A2 | 2/1992 | (EP) . |
| 0756878A2 | 2/1997 | (EP) . |
| WO 99/24114 | 5/1999 | (WO) . |

OTHER PUBLICATIONS

Stickney, R.E., et al., "Shock Advised!" –LIFEPAK AEDs incorporate vital rhythm analysis system, In Sync, Physio–Control Corporation, Spring/Summer 1997, pp. 20–21.

Aronson, A.L., et al., The Automatic External Defibrillator–pacemaker: Clinical Rationale and Engineering Design, Medical Instrumentation, 1986, vol. 20, pp. 27–35.

Diack, A.W., et al., An automatic cardiac resuscitator for emergency treatment of cardiac arrest, Medical Instrumentation, 1979, vol. 13, pp. 78–83.

(List continued on next page.)

*Primary Examiner*—Kennedy Schaetzle
(74) *Attorney, Agent, or Firm*—Christensen O'Connor Johnson Kindness PLLC

(57) ABSTRACT

A medical device (e.g., an automated external defibrillator) automatically detects and reports cardiac asystole by first obtaining ECG data and calculating one or more ECG measures from the ECG data. The defibrillator evaluates the ECG data by classifying the ECG data into a class indicative of cardiac condition, wherein one class is indicative of cardiac asystole. If the defibrillator classifies the ECG data into the class indicative of cardiac asystole, the defibrillator reports the asystole classification on a display. The defibrillator may classify the ECG data into a rhythm class associated with a cardiac rhythm, such as asystole, and report the rhythm class of the ECG data on the display. The defibrillator may also suggest a procedure to undertake, such as a therapy (e.g., defibrillation for a shockable cardiac rhythm), based on the classification of the ECG data. The defibrillator may reserve reporting the detection of asystole until a predetermined number of ECG classifications over at least a predetermined period of time have resulted in an asystole classification. The defibrillator may also reserve reporting the detection of asystole until an ECG classification resulting in asystole has been performed outside of a predetermined period of time after application of a defibrillation pulse. A statistical binary classification and regression tree may be used to classify the ECG data according to cardiac rhythm. Other signal data, such as impedance or phonocardiographic signal data, may also be obtained and classified with the ECG data.

64 Claims, 18 Drawing Sheets

U.S. PATENT DOCUMENTS

| | | | |
|---|---|---|---|
| 4,619,265 | * 10/1986 | Morgan et al. | 607/6 |
| 4,919,144 | 4/1990 | Vandehey . | |
| 5,002,052 | 3/1991 | Haluska . | |
| 5,251,625 | 10/1993 | Wilson et al. . | |
| 5,262,944 | * 11/1993 | Weisner et al. | 600/300 |
| 5,366,487 | 11/1994 | Adams et al. . | |
| 5,379,776 | 1/1995 | Murphy et al. . | |
| 5,391,187 | 2/1995 | Freeman . | |
| 5,405,362 | 4/1995 | Kramer et al. . | |
| 5,456,261 | * 10/1995 | Luczyk | 600/515 |
| 5,474,574 | 12/1995 | Payne et al. . | |
| 5,507,778 | 4/1996 | Freeman . | |
| 5,518,001 | 5/1996 | Snell . | |
| 5,571,142 | 11/1996 | Brown et al. . | |
| 5,623,936 | 4/1997 | McClure . | |
| 5,632,766 | 5/1997 | Hsu et al. . | |
| 5,724,983 | * 3/1998 | Selker et al. | 600/301 |
| 5,819,007 | * 10/1998 | Elghazzawi | 395/51 |

OTHER PUBLICATIONS

Rozkovec, A., et al., Safety and Effectiveness of a Portable External Automatic Defibrillator–Pacemaker, Clinical Cardiology, 1983, vol. 6, pp. 527–533.

Duman, I., et al., A Computerized System for the Analysis of Cardiac Rhythm and Conduction, Proceedings: Computers in Cardiology, IEEE Computer Society Press, Los Alamitos, California, 1991, pp. 441–443.

* cited by examiner

US 6,304,773 B1

AUTOMATIC DETECTION AND REPORTING OF CARDIAC ASYSTOLE

RELATED APPLICATION

This application claims the benefit of the filing date of U.S. provisional application Serial No. 60/086,564, filed May 21, 1998, as provided by 35 U.S.C. §119(e).

FIELD OF THE INVENTION

The present invention relates generally to the monitoring and analysis of cardiac activity, and more particularly, to the analysis of non-invasive signals indicative of cardiac condition to enhance triage and patient treatment decisions.

BACKGROUND OF THE INVENTION

Automated external defibrillators (AEDs) are generally able to monitor and analyze electrocardiogram (ECG) data obtained from a patient and determine whether the patient's ECG indicates a "shockable" or "non-shockable" cardiac rhythm (i.e., a cardiac rhythm that may be treated with a defibrillation pulse). Commonly accepted medical protocol recommends treating certain cardiac rhythms, such as ventricular fibrillation (VF) and pulseless ventricular tachycardia (VT), with rapid application of a defibrillation pulse. On the other hand, potentially perfusing cardiac rhythms are generally not treated by application of a defibrillation pulse. These "non-shockable" rhythms include those with QRS complexes being present, such as supraventricular tachycardia and bradycardia. Cardiac asystole (i.e., a lack of cardiac activity) is also considered to be "non-shockable," since a shock provides no benefit during asystole.

An AED typically obtains ECG data from a patient through electrodes placed on the patient. The AED evaluates the ECG data and makes a binary shock/no-shock decision based on the ECG evaluation. The AED then reports the shock/no-shock decision to the operator of the AED. If the AED detects a VF or VT cardiac rhythm in the patient, for example, the AED typically reports "Shock Advised" on a display, charges a defibrillation capacitor inside the defibrillator, and when instructed by the operator of the AED, delivers a defibrillation pulse from the capacitor to the patient. If, on the other hand, the AED detects a non-shockable cardiac rhythm (e.g., asystole or a rhythm with QRS complexes), the AED simply reports "No Shock Advised." As noted, cardiac asystole represents the absence of electrical activity in the heart. Cardiac asystole may be found initially in a patient, it may develop over time during a resuscitation effort, or it may occur for some time after a defibrillation shock. Defibrillation therapy is generally neither effective nor indicated in the treatment of asystole. Chest compressions and artificial respirations (i.e., cardiopulmonary resuscitation, or CPR) may be performed on the patient, but normally are not effective in treating asystole when it is the initial rhythm. As noted by the American Heart Association (AHA) in its Textbook of Advanced Cardiac Life Support (1994), asystole unfortunately "most often represents a confirmation of death rather than a rhythm to be treated."

The AHA encourages medical directors of pre-hospital care to establish criteria for those providing basic life support in the field to determine when to cease providing treatment, including defibrillation, to a patient, particularly in circumstances where a lack of resources and/or risk to rescuers from continuing to treat the patient outweigh the likelihood of successful resuscitation. Such risks include the risk of vehicular accidents during high-speed emergency transport and the risk of withholding basic life support from another patient needing medical assistance in favor of continuing to attempt to resuscitate the patient in an asystolic condition.

A caregiver providing basic life support to a patient may not recognize when the patient's heart is in an asystolic condition. At the present time, AEDs are intended for use by minimally-trained responders and indicate whether delivery of a defibrillation pulse is advised, but do not identify specific ECG rhythms. Without knowing when a patient's heart is in an asystolic condition, a caregiver may continue to apply basic life support techniques, such as defibrillation and CPR, to a patient for a time longer than is medically useful and perhaps to the risk of self and others. In addition, without the ability to recognize cardiac asystole, a caregiver is also not able to perform meaningful triage.

SUMMARY OF THE INVENTION

The present invention provides methods and an apparatus for evaluating ECG data to automatically detect and report a cardiac condition, such as cardiac asystole. In one exemplary embodiment, the invention is implemented in a defibrillator which obtains ECG data and calculates one or more ECG measures from the ECG data. The defibrillator classifies ECG data in multiple classifiers using the one or more ECG measures. Each classifier of the multiple classifiers classifies the ECG data into a class indicative of cardiac condition. One class indicative of cardiac condition is indicative of cardiac asystole. If the defibrillator classifies the ECG data in the class indicative of cardiac asystole, the defibrillator reports the detection of asystole on its display.

The defibrillator may obtain and classify a single segment of ECG data multiple segments of ECG data. Alternatively, the defibrillator may obtain ECG data continuously and classify the ECG data at one or more instances in time. If classifying multiple segments of ECG data, the defibrillator determines and reports an overall ECG classification based on a consensus (e.g., two out of three) of the classification of each segment.

In one aspect, the defibrillator may use a statistical binary classification and regression tree to classify the ECG data. The classification and regression tree implements a series of binary decision rules to systematically classify the ECG into a particular class. For instance, the defibrillator may classify the ECG data into a rhythm class associated with a cardiac rhythm. The binary decision rules of the classification and regression tree systematically classify ECG data of unknown rhythm type into a particular rhythm class.

In implementations where the defibrillator classifies the ECG data according to cardiac rhythm, the defibrillator may report the rhythm class into which the ECG data is classified. The defibrillator may also automatically prompt on its display a procedure to undertake based on the rhythm class into which the ECG data is classified. The procedure to be undertaken may be a therapy associated with the rhythm class of the ECG data, such as a defibrillation pulse for ECG data classified as a shockable cardiac rhythm. The procedure may also be determining and displaying an instruction providing guidance for prioritizing the delivery of a therapy.

In another aspect of the invention, the outcome of an ECG evaluation (i.e., the overall ECG classification) is recorded in a history of ECG evaluations stored in memory. When cardiac asystole is detected, the history of ECG evaluations is reviewed to determine whether a predetermined number of ECG evaluations over a predetermined period of time resulted in detection of asystole. If so, cardiac asystole is reported. If not, a no-shock advisory may be prompted on the display without reporting cardiac asystole. In this manner, asystole is reported only when the asystolic condition is persistent. Identifying persistent asystole is particularly useful to first-responding caregivers performing triage in emergency situations.

In still another aspect of the invention, if the ECG data is classified as cardiac asystole, the defibrillator determines whether a defibrillation pulse has been delivered to the patient within a predetermined time period. Since a period of asystole may occur following the delivery of a defibrillation pulse, the defibrillator reports cardiac asystole only if asystole is detected outside the predetermined time period following delivery of a defibrillation pulse.

As an alternative to classifying ECG data using multiple classifiers, a medical device configured according to the invention may use a single classifier, such as a statistical binary classification and regression tree, to directly classify the ECG as shockable, asystole, or non-asystole. If the classifier classifies the ECG data into one of a plurality of rhythm classes, the rhythm classes associated with shockable cardiac rhythms are treated as a shockable classification. Rhythm classes indicating asystole or noisy asystole are treated as an asystole classification. Any remaining rhythm classes in the plurality of rhythm classes are treated as non-asystole. Depending on the rhythm class into which the ECG data is classified, the medical device may suggest a particular therapy (such as advising a defibrillation pulse if a shockable rhythm is detected). A no-shock advisory is provided for asystole and non-asystole classifications, along with a report of cardiac asystole if the ECG evaluation results in an asystole classification.

In accordance with a recommendation of the International Liaison Committee on Resuscitation (ILCOR), the medical device (e.g., defibrillator) implementing the present invention may set a flag if the ECG data is (1) classified into a rhythm class indicative of cardiac perfusion, and (2) if the ECG data is also classified into a rhythm class associated with a non-shockable cardiac condition. The flag indicates that on subsequent delivery of a defibrillation pulse to the patient, the subsequent defibrillation pulse should convey an amount of energy equal to the energy conveyed in the most recently delivered defibrillation pulse (if there was one).

In still a further aspect of the invention, signal data indicative of cardiac condition other than ECG data may also be obtained from a patient. A medical device implementing the present invention receives and evaluates the signal data with the ECG data in order to classify the signal data and ECG data into a class indicative of cardiac condition. The medical device automatically reports an asystole classification on the display if the signal data and ECG data are classified into a class indicative of cardiac asystole. The medical device may also automatically charge one or more defibrillation capacitors for delivery of a defibrillation pulse if the signal data and ECG data are classified into a class indicative of a shockable cardiac condition. The medical device may provide an instruction on the display based on the classification of the signal data and ECG data for guiding a first-responding caregiver in providing emergency triage and treatment of the patient without the benefit of human intervention.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
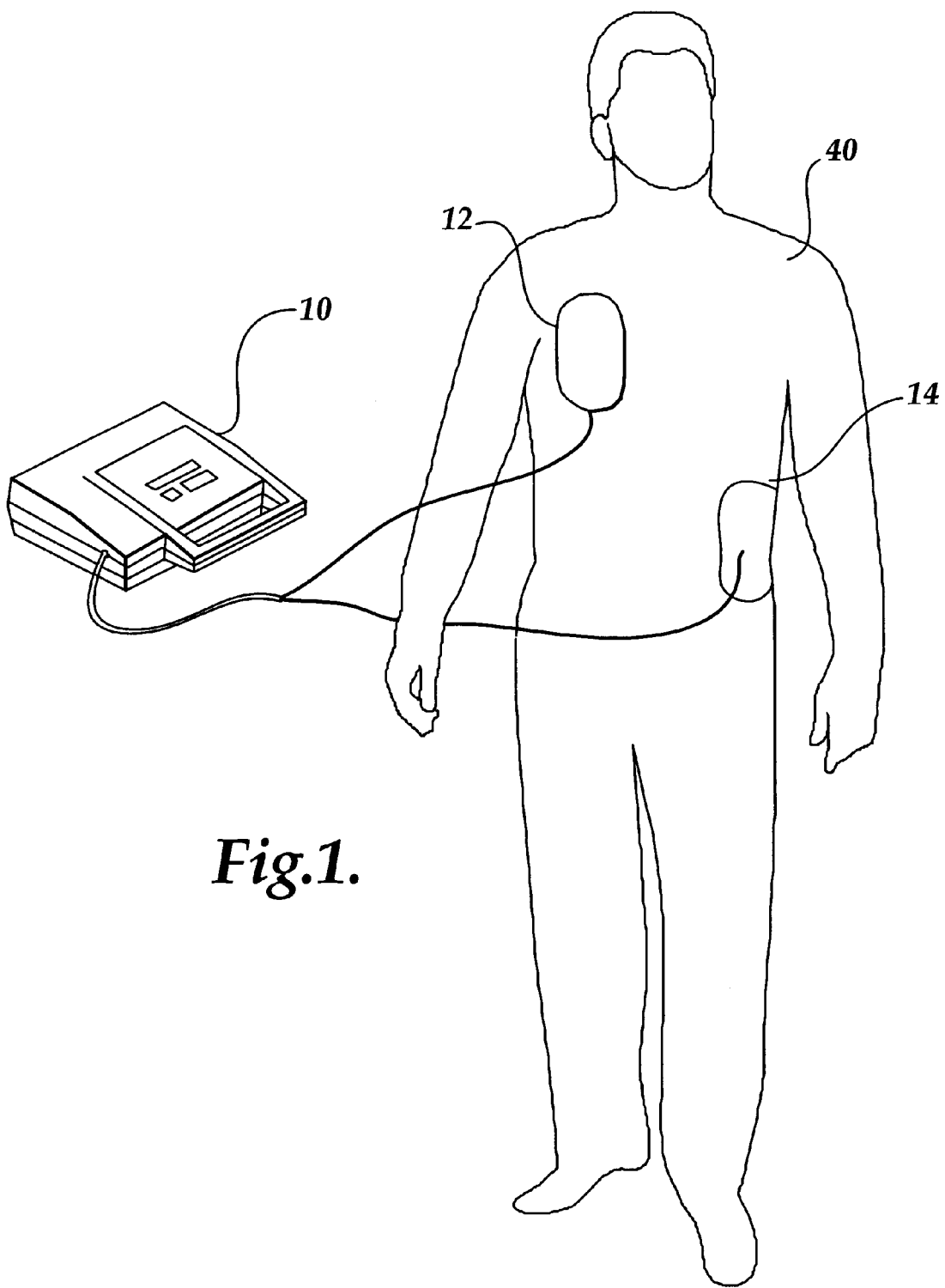
FIG. 1 depicts an external defibrillator configured to operate in accordance with the present invention with a pair of monitoring/defibrillation electrodes attached to a patient.

FIG. 1 depicts an external defibrillator 10 that automatically detects and reports cardiac condition, such as cardiac asystole, in accordance with the present invention. When the defibrillator 10 is attached to a patient 40 via a plurality of monitoring/defibrillation electrodes 12 and 14, the defibrillator 10 obtains non-invasive signals indicative of the patient's cardiac condition, such as the patient's ECG signals, and automatically evaluates the signals to detect and report cardiac asystole. While FIG. 1 shows the invention implemented in a defibrillator 10, it should be understood that the invention may alternatively be implemented in a standalone ECG monitoring device or other medical device that acquires and analyzes non-invasive signals indicative of cardiac condition.

The two electrodes 12 and 14 shown in FIG. 1 are attached to the skin of the patient 40 on the patient's torso. The first electrode 12 is shown attached to the upper right torso area of the patient 40. The second electrode 14 is shown attached to the lower left torso area toward the side of the patient. ECG signals sensed by the electrodes 12 and 14 placed at these locations are used to produce a lead of ECG data. One lead of ECG data known in the art is called the sternum-apex (SA) lead (also known as the anterior-apex lead). The SA lead has an ECG morphology somewhat comparable to a lead II produced by a standard 12-lead ECG system. Techniques for producing an SA lead and techniques for producing other leads, such as a lead II in a 12-lead ECG system, are well-known to those having ordinary skill in ECG technology and do not form part of this invention.

Moreover, FIG. 1 illustrates only suggested locations for placing the electrodes 12 and 14 on the patient 40. The electrode 12 may alternatively be placed, for example, on the patient's chest area closer to the heart, with the electrode 14 placed on the patient's back. A device formed according to the present invention may also use more electrodes than the two electrodes 12 and 14 shown in FIG. 1, and may include other monitoring elements, such as phonocardiograph tranducers and reflectance oximetry sensors. The electrodes 12 and 14 may also be configured in a conventional manner for sensing patient impedance. Regardless of the number of electrodes used and types of sensors included, one or more channels of signal data, in this case one or more leads of ECG data such as the SA lead, are derived using conventional techniques from the signals sensed by the electrodes.

Figure 2:
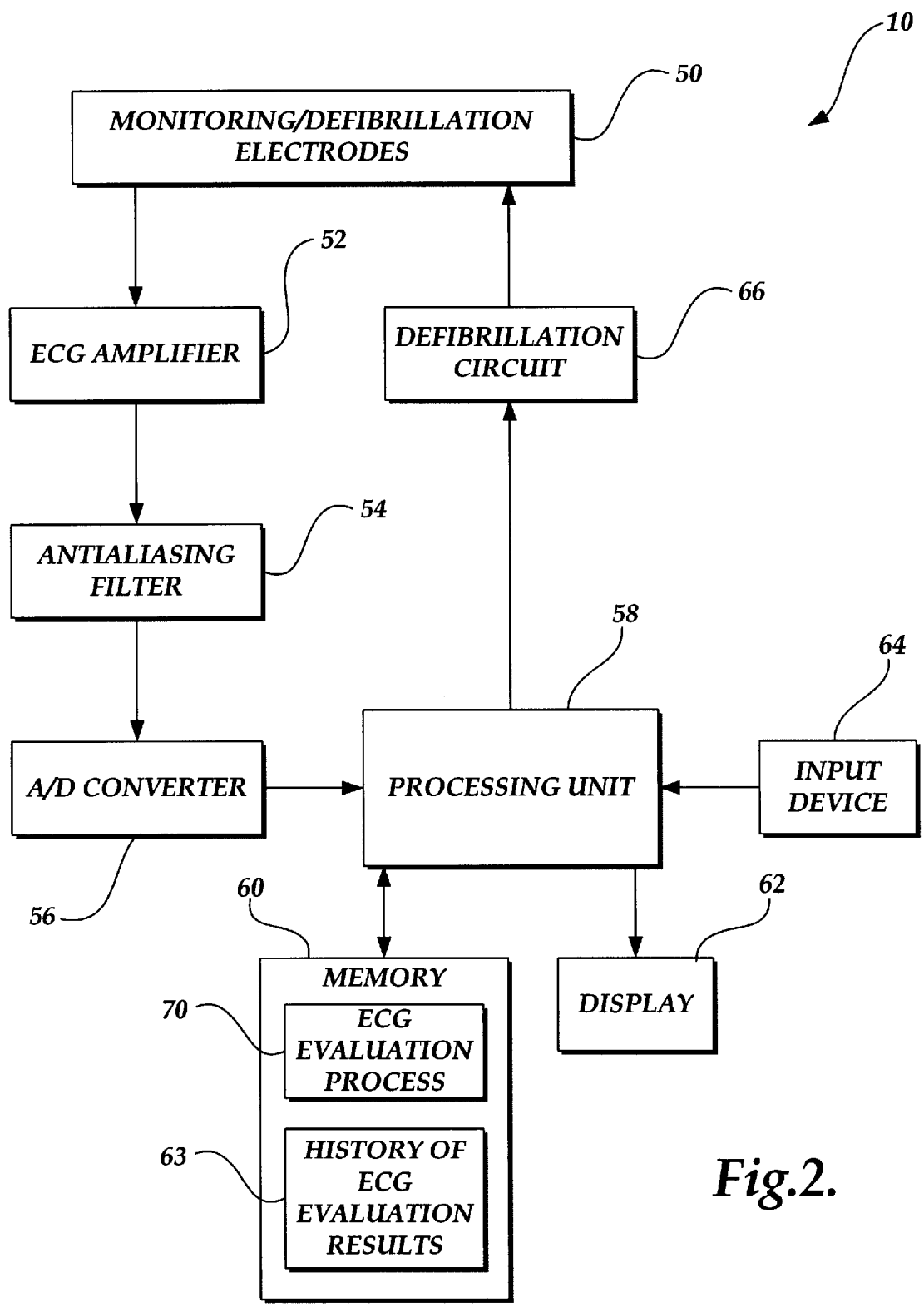
FIG. 2 is a block diagram illustrating the major components of the defibrillator shown in FIG. 1.

FIG. 2 illustrates in more detail the major components of the defibrillator 10 shown in FIG. 1. In FIG. 2, ECG signals sensed by monitoring/defibrillation electrodes 50 (e.g., electrodes 12 and 14) are provided to an ECG amplifier 52. The ECG amplifier 52 both amplifies and filters the ECG signals. The ECG amplifier 52 may amplify the ECG signals by a factor of 1,000 or more to enable the circuitry of the defibrillator 10 to analyze the ECG signals.

The ECG amplifier 52 filters the ECG signals to eliminate noise and other signal contaminants. In one actual embodiment of the defibrillator 10, the ECG amplifier 52 includes a low-pass filter that attenuates high frequency signals (e.g., frequencies above 30 Hertz) and a high-pass filter that attenuates low frequency signals (e.g., frequencies below about 2.5 Hertz). Alternative embodiments of the invention may include different signal filtering to adapt the device for use in particular environments. Signal filtering may also be limited to ECG signals used to calculate certain ECG measures, such as average amplitude and average frequency, that are discussed in more detail below.

The ECG amplifier 52 provides the amplified, filtered ECG signals to an anti-aliasing filter 54. The anti-aliasing filter 54 is designed to limit aliasing introduced in the ECG signals by the subsequent analog-to-digital conversion performed by the A/D converter 56. The bandwidth of the anti-aliasing filter 54 is dictated in part by the sampling rate of the A/D converter 56. In one actual embodiment of the defibrillator 10, the ECG signals are sampled by the A/D converter 56 at a 120 Hz rate. The A/D converter 56 converts the ECG signals into digitized ECG data that are then provided to a processing unit 58 for evaluation. The construction of anti-aliasing filters and A/D converters are well known in the art and in many cases are readily available in off-the-shelf devices.

The processing unit 58 evaluates the ECG data by implementing an ECG evaluation process 70 described in more detail below. In one implementation of the present invention, the ECG evaluation process 70 determines and reports whether the ECG data indicates a shockable or non-shockable cardiac rhythm, and if non-shockable, whether the ECG data indicates cardiac asystole. The processing unit 58 preferably comprises a computer processor that operates in accordance with programmed instructions stored in memory 60 that carry out the ECG evaluation process 70.

The processing unit 58 reports the results of the ECG evaluation process 70 to the operator of the defibrillator 10 via a display 62. The display 62 may include, for example, lights, audible signals or speech, a printer, and/or a display screen (e.g., LCD or AMLCD). The processing unit 58 may also receive input from the operator of the defibrillator 10 via an input device 64. The input device 64 may include one or more keys, knobs, buttons, or other types of user input devices. The processing unit 58 preferably records the results of the ECG evaluation process 70 in a history of ECG evaluation results 63 stored in memory 60.

If, while performing the ECG evaluation process 70, the processing unit 58 detects a shockable cardiac rhythm, the processing unit 58 instructs a defibrillation circuit 66 to commence preparation to deliver a defibrillation pulse to the patient. In that regard, the defibrillation circuit 66 charges one or more defibrillation capacitors internal to the defibrillation circuit 66. When the defibrillation charge is ready for delivery, the processing unit 58 advises the operator (via the display 62) that the defibrillator 10 is ready to deliver the defibrillation pulse.

Preferably, the processing unit 58 asks the operator to initiate the delivery of the pulse. When the operator initiates delivery of the defibrillation pulse (e.g., by initiating the input device 64), the processing unit 58 instructs the defibrillation circuit 66 to discharge the energy stored in the defibrillation capacitors through the monitoring/defibrillation electrodes 50 attached to the patient. Alternatively, the processing unit 58 may cause the defibrillation circuit 66 to automatically deliver the defibrillation pulse when specified conditions (e.g., expiration of a predetermined period of time, acceptable patient impedance, etc.) are met.

While FIG. 2 illustrates the major components of the defibrillator 10, those having ordinary skill in ECG/defibrillation technology will appreciate that the defibrillator 10 may contain other components than those shown in FIG. 2. However, the disclosure of a preferred embodiment of the present invention does not require that all of these general conventional components be shown. The present invention may also be implemented in a cardiac monitor having essentially the same components illustrated in FIG. 2 except that the monitor does not have the components necessary for delivering a defibrillation pulse. In that regard, the cardiac monitor is configured to prompt the user with messages reporting the patient's condition.

Figure 3:
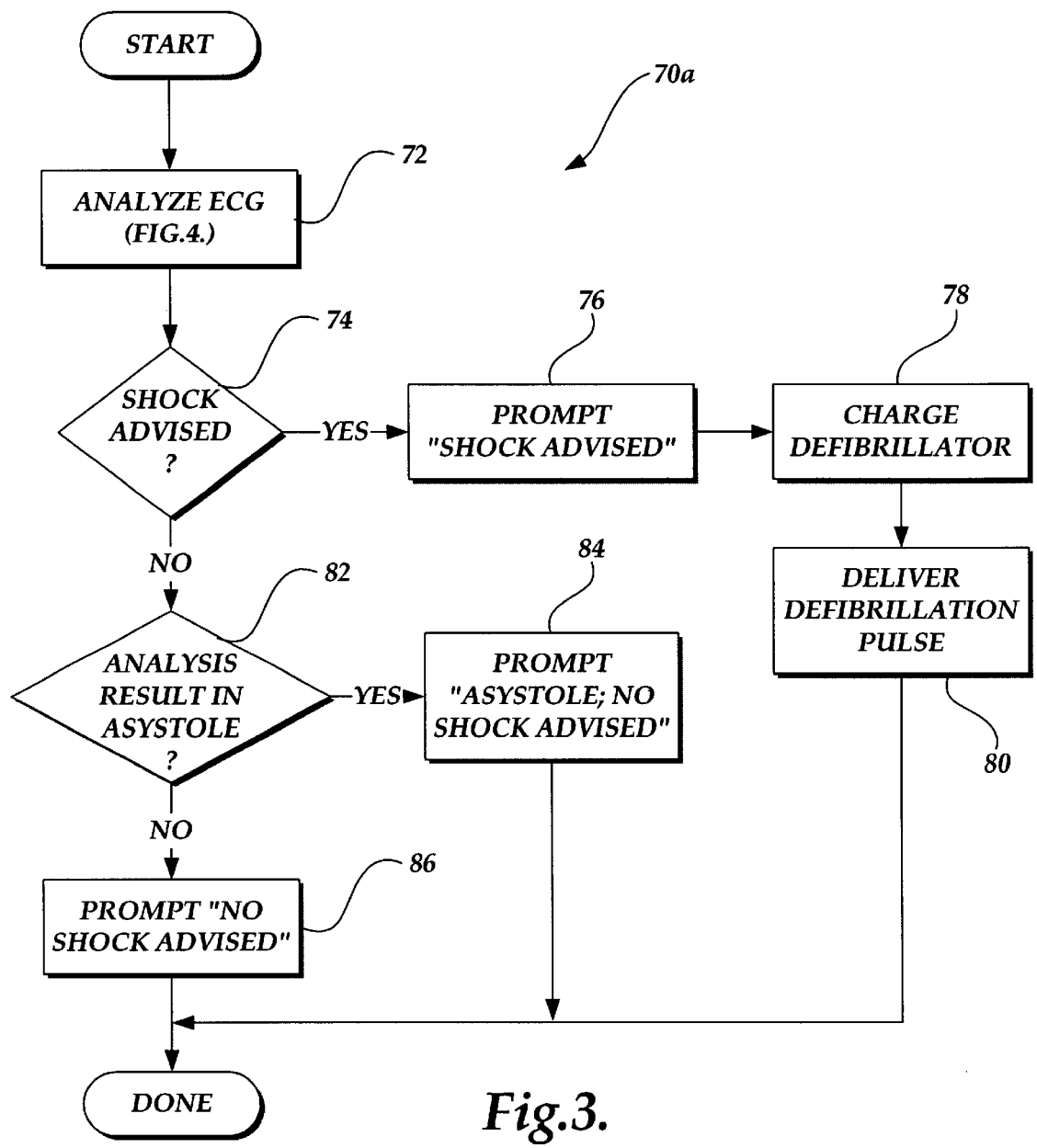
FIG. 3 is a flow diagram illustrating one version of an ECG evaluation process used by the defibrillator shown in FIG. 1 to detect and report cardiac asystole in accordance with the present invention.

The defibrillator 10 may implement the ECG evaluation process 70 in a variety of ways. One version 70a of the ECG evaluation process 70 is illustrated in FIG. 3. The ECG evaluation process 70a begins in a block 72 by analyzing a patient's ECG. The ECG analysis performed in block 72 includes obtaining a segment of ECG data from a patient, calculating one or more ECG measures from the ECG data, and analyzing the ECG measures to classify the patient's ECG as indicating a shockable or non-shockable rhythm, and if non-shockable, then as indicating asystole or non-asystole. One procedure for performing the ECG analysis in block 72 is illustrated in greater detail in FIG. 4.

Figure 4:
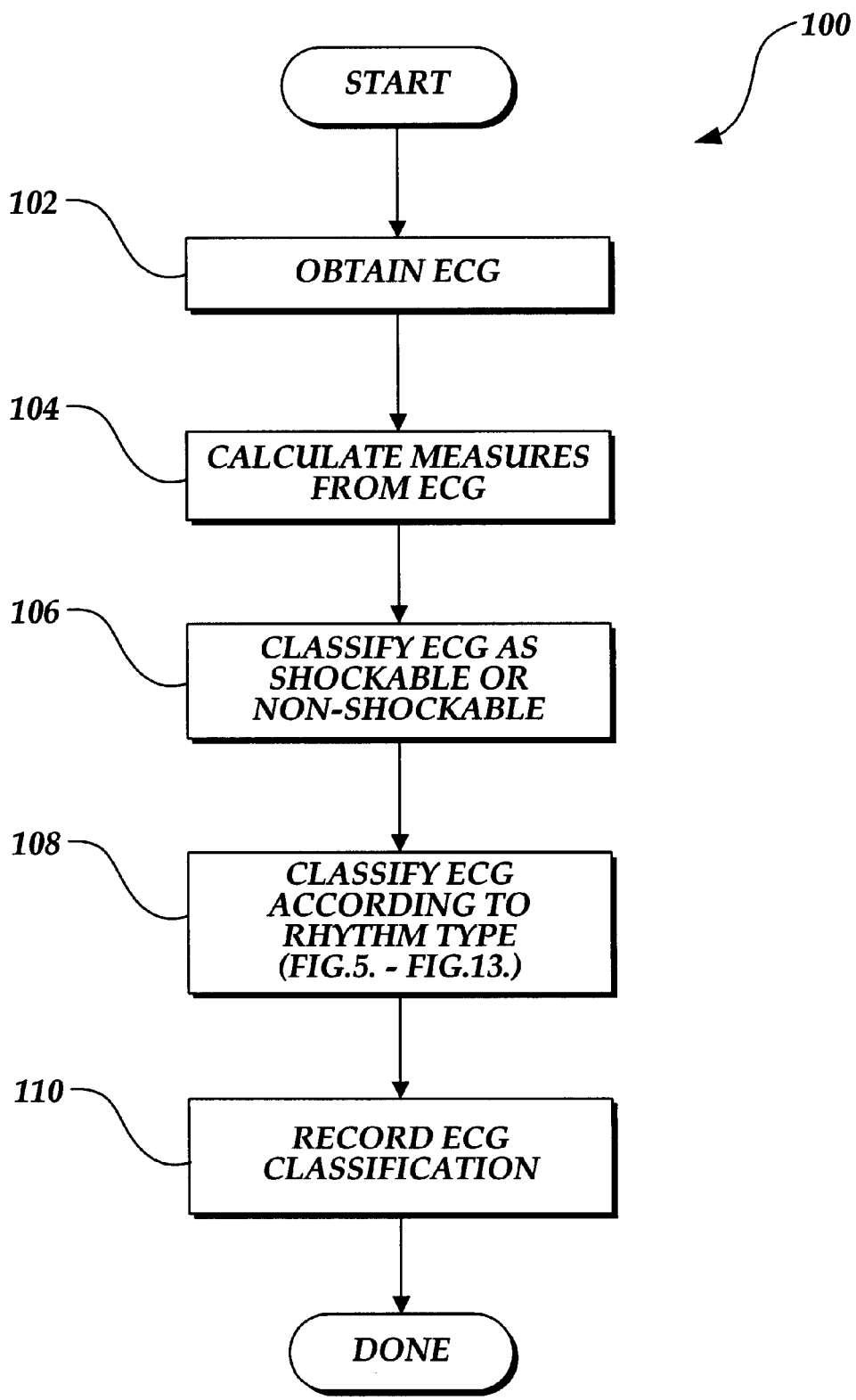
FIG. 4 is a flow diagram illustrating an ECG analysis process for analyzing and classifying ECG data obtained from a patient for use in the ECG evaluation process shown in FIG. 3.
Figure 5:
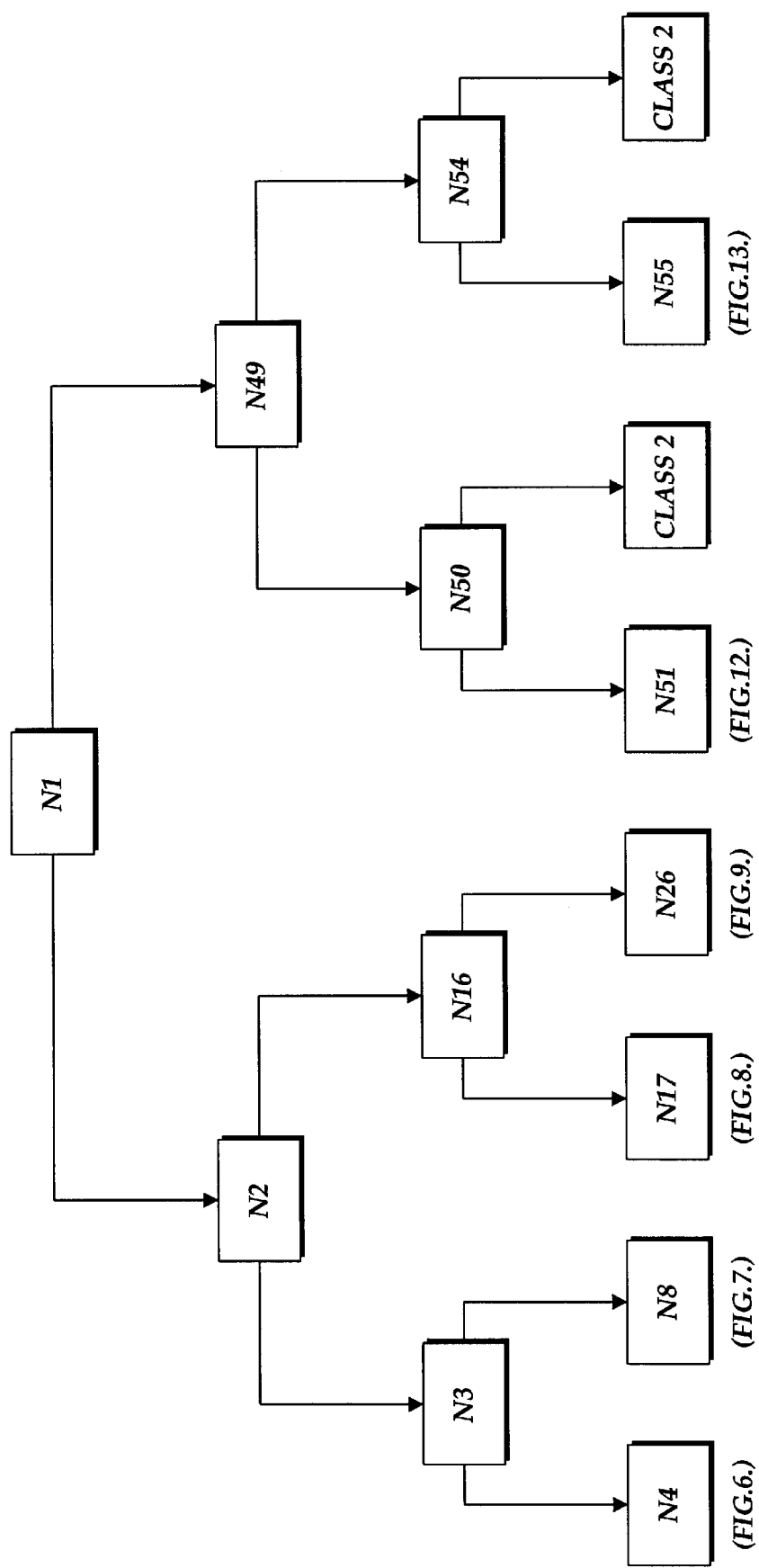
FIGS. 5–13 illustrate a classification and regression tree used by the ECG analysis process shown in FIG. 4 to classify ECG data as indicating a particular type of cardiac rhythm.
Figure 6:
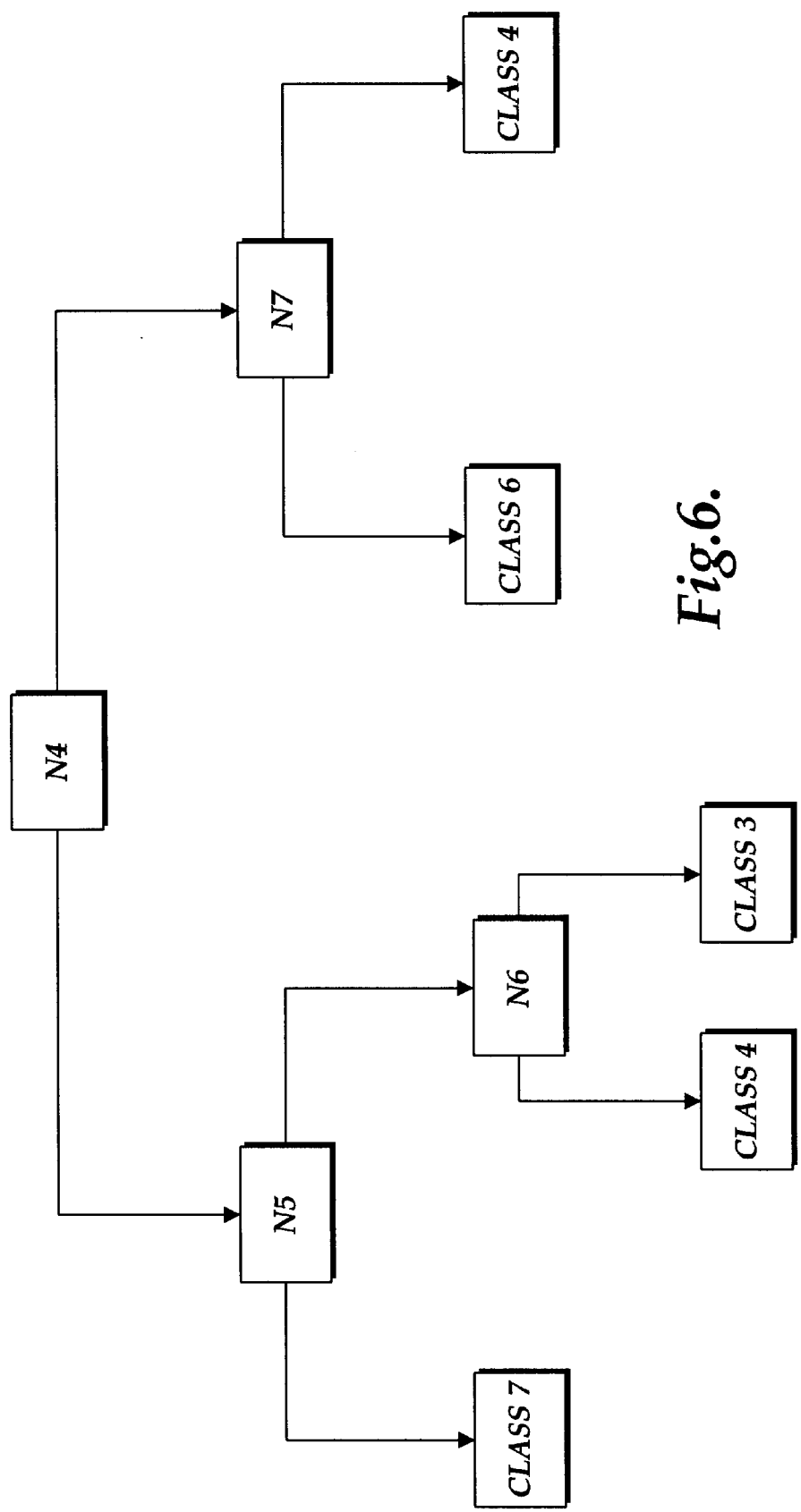
Figure 7:
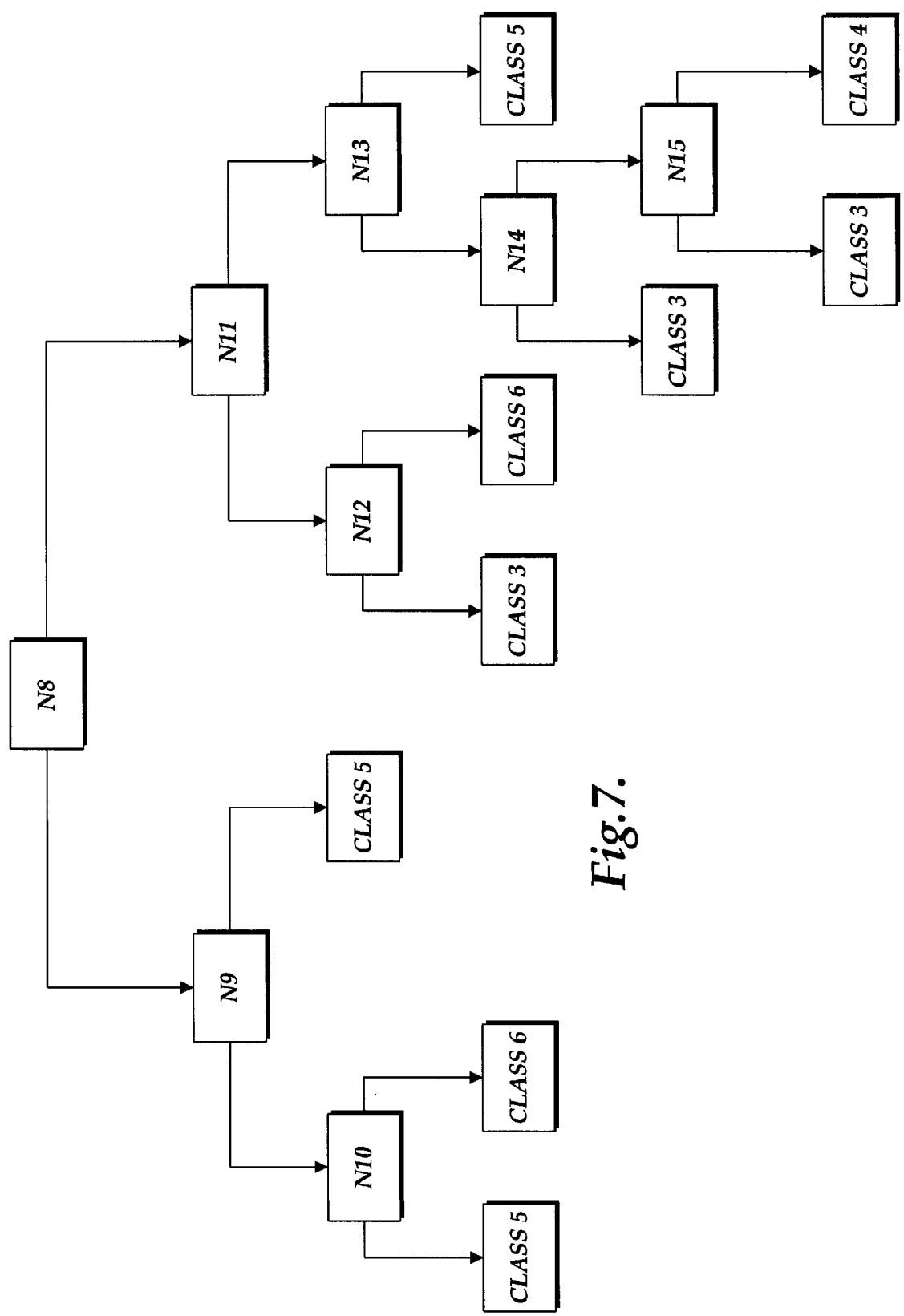
Figure 8:
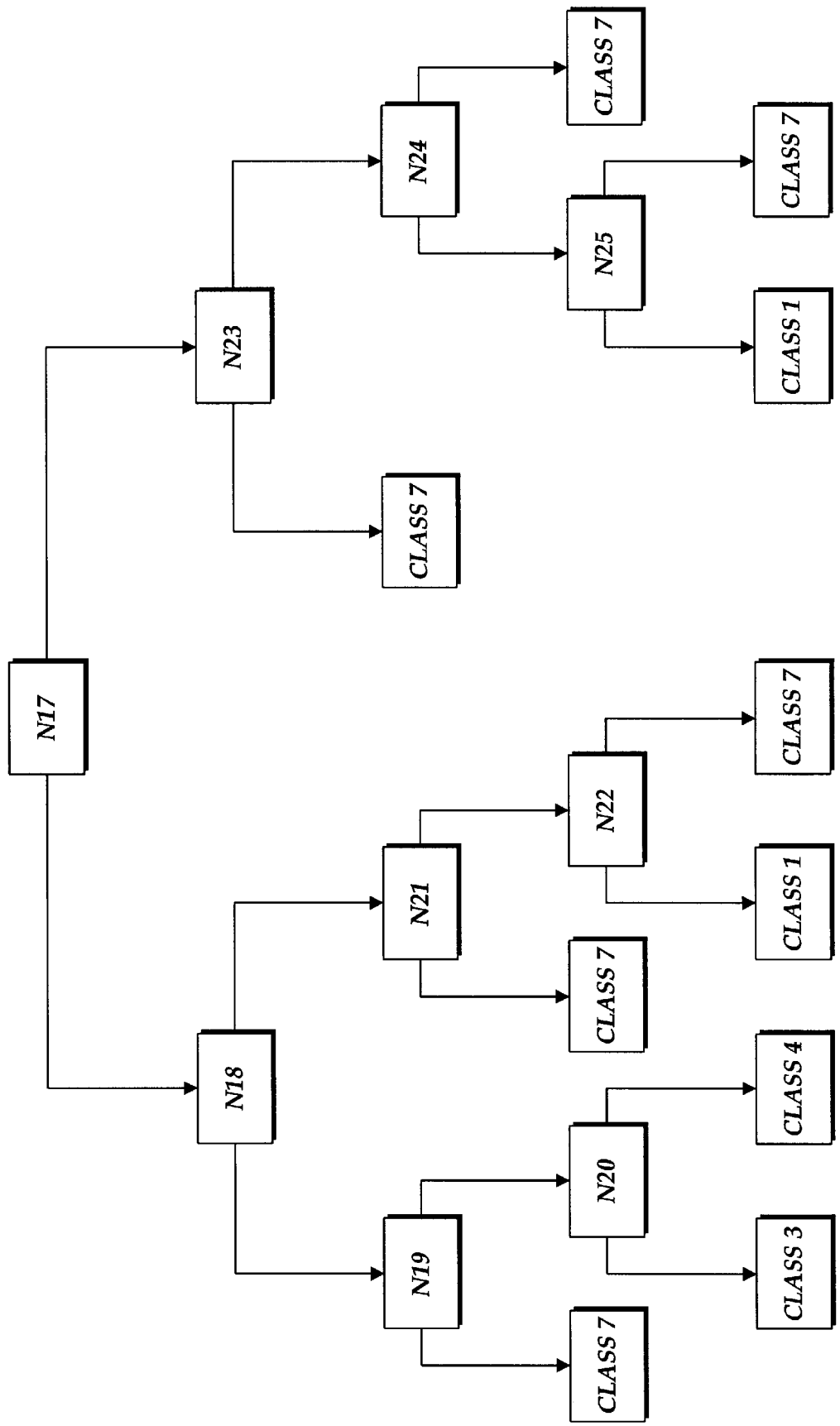
Figure 9:
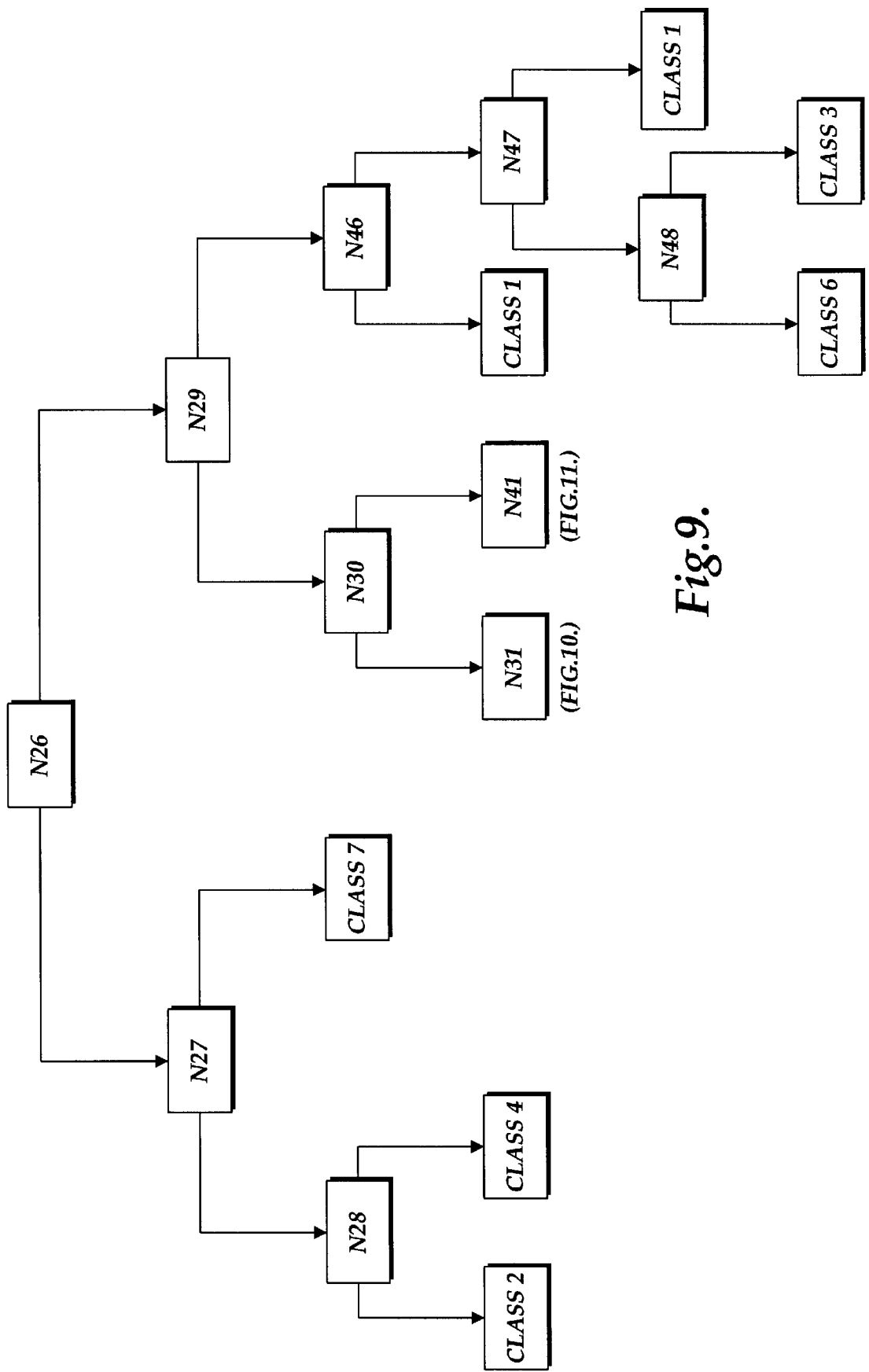
Figure 10:
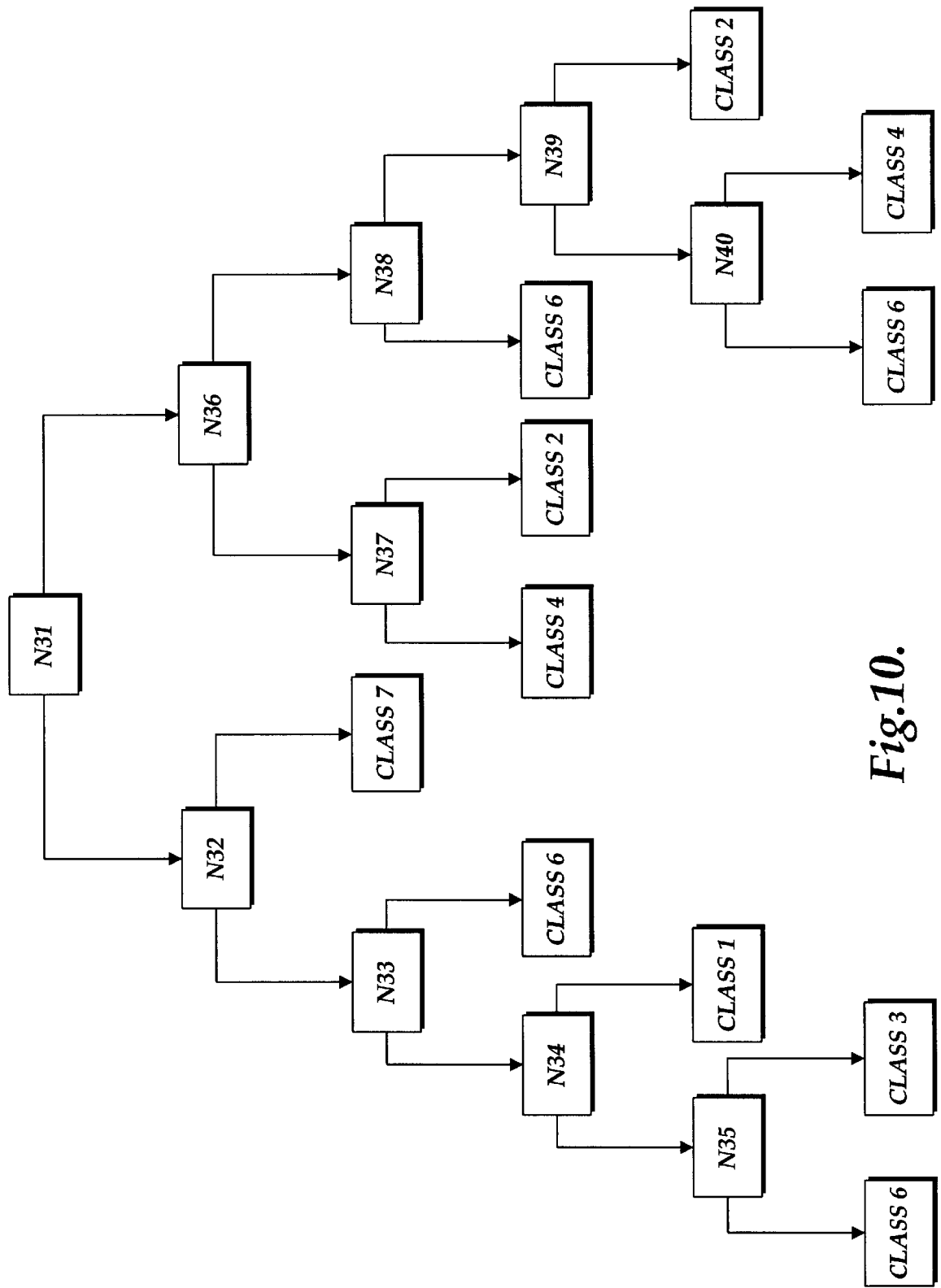
Figure 11:
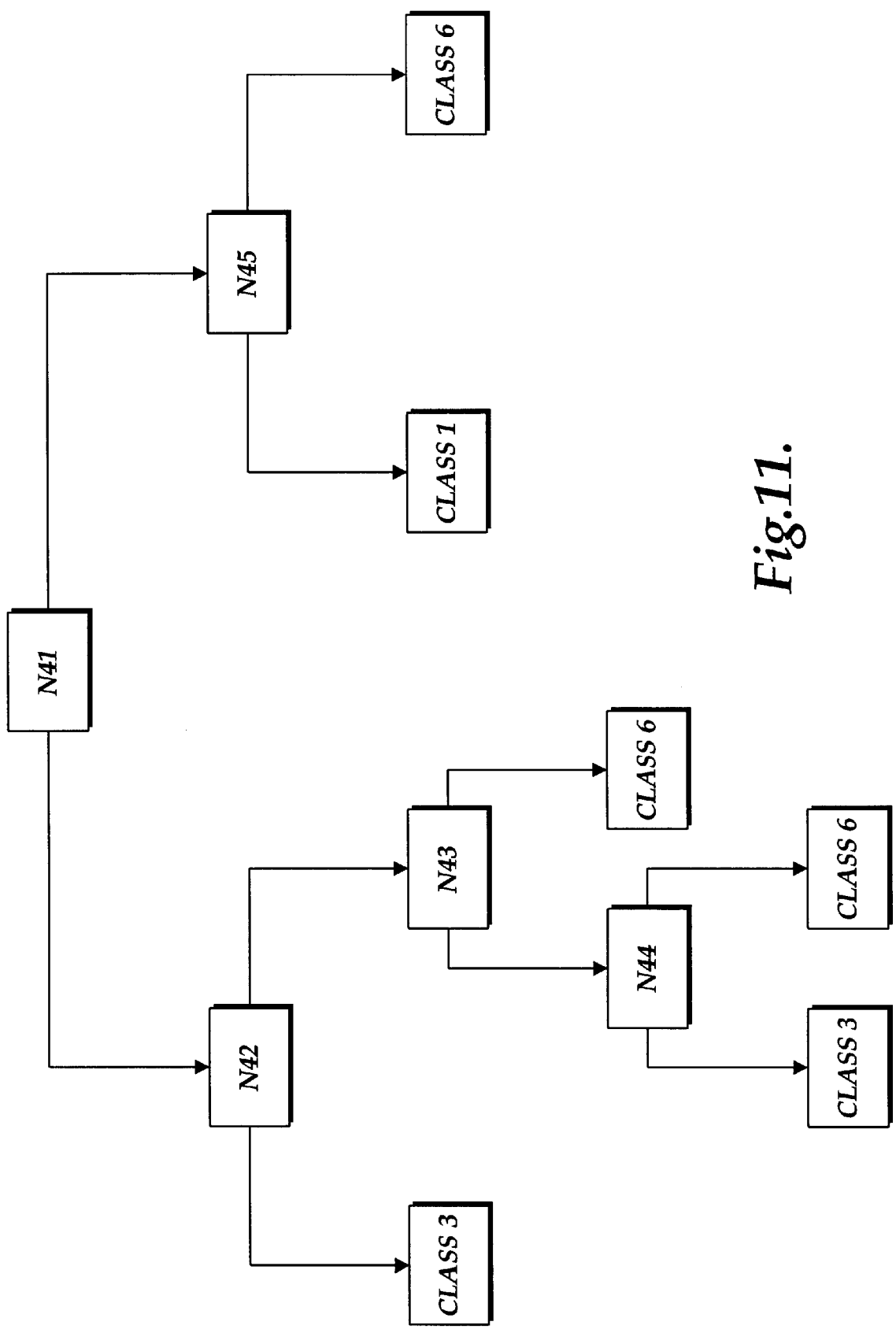
Figure 12:
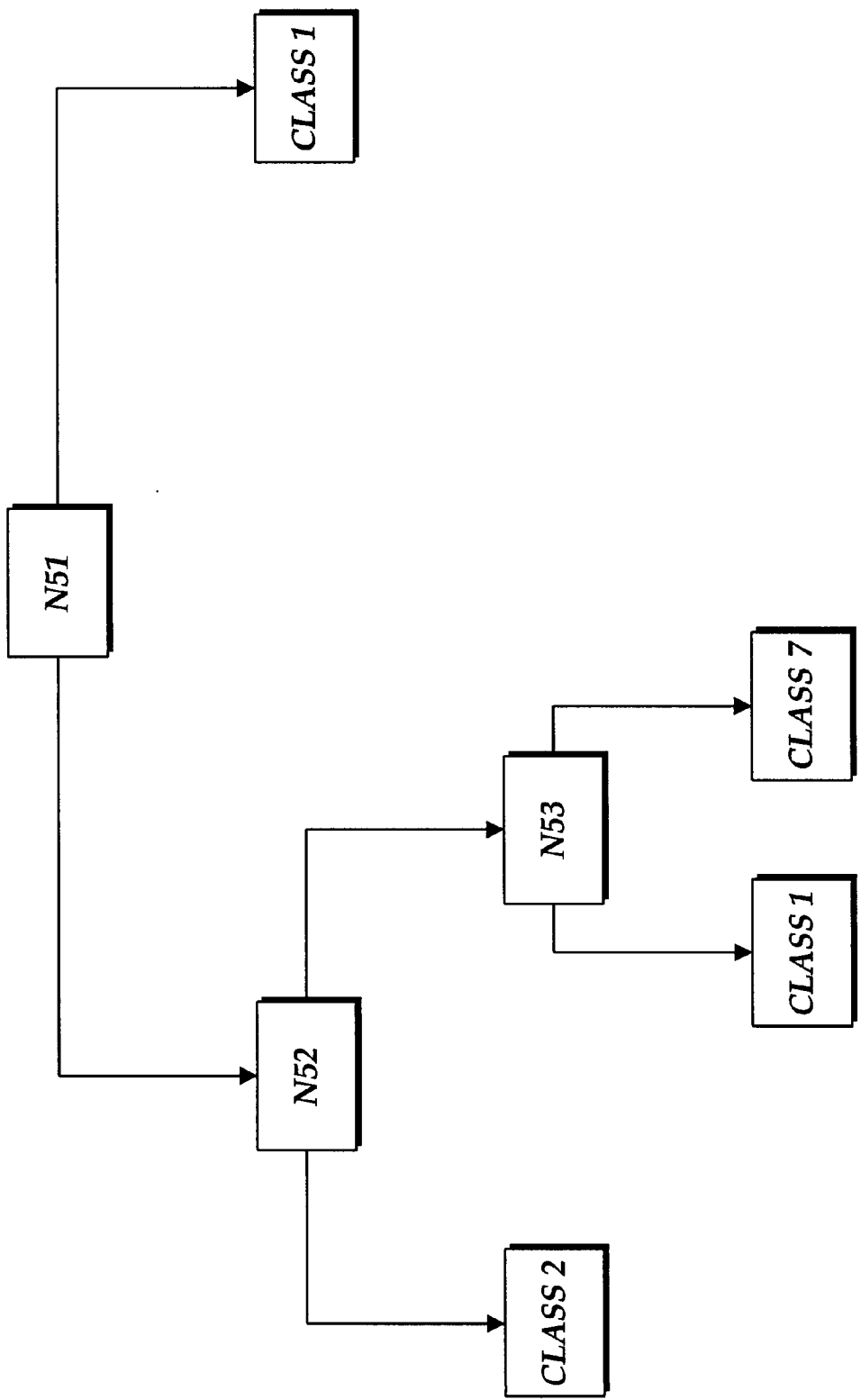
Figure 13:
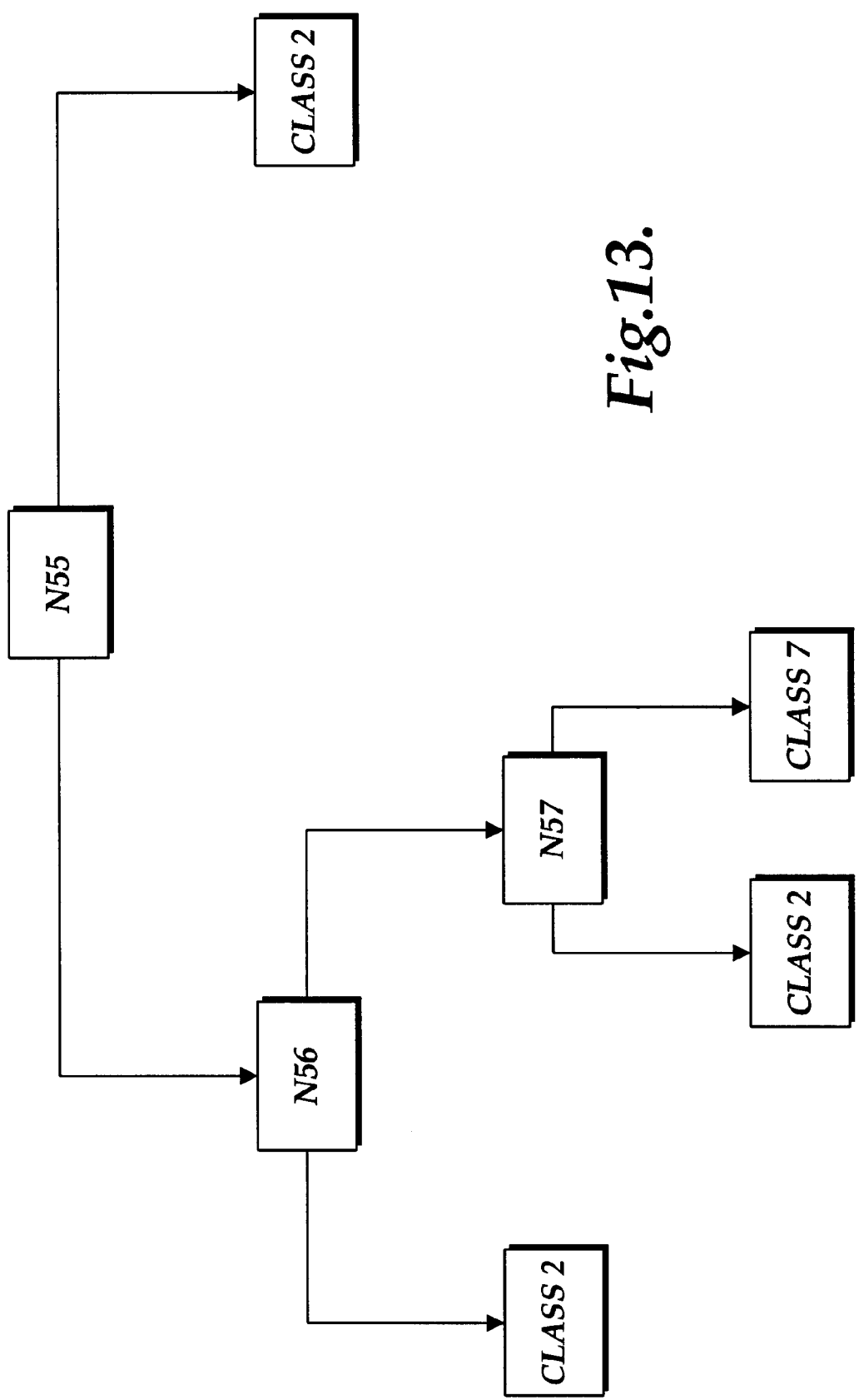

Turning to FIG. 4, the defibrillator 10 begins the ECG analysis procedure 100 in a block 102 by obtaining one or more leads of ECG data from a patient. As noted earlier, a lead of ECG data, such as an SA lead, is derived from ECG signals sensed by monitoring/defibrillation electrodes (e.g., electrodes 12 and 14) that are placed on the patient. One actual embodiment of the defibrillator 10 obtains a 2.7-second segment of ECG data. Of course, other embodiments of the present invention may obtain a longer or shorter segment of ECG data, or may evaluate ECG data on a continuous basis through the use of one or more continuous filters and classifiers. In a block 104, the defibrillator 10 calculates one or more measures from the segment of ECG data that are later used to classify the patient's ECG.

In one actual embodiment of the defibrillator 10, five ECG measures are calculated in block 104. These five measures include baseline content, average amplitude, average frequency, R-wave count, and ECG rate, which are next described in more detail.

The baseline content of an ECG is a measure of the ratio of low-slope ECG data to high-slope ECG data. Low-slope ECG data is generally indicative of a flat baseline in the patient's ECG while high-slope ECG data is generally indicative of a QRS complex. Low-slope and high-slope ECG data may be determined by first dividing the segment of ECG data into smaller portions (e.g., at points within the ECG where the slope of the ECG data changes from positive to negative or vice versa). The slope of each of these smaller portions is then calculated. The number of portions having low slopes compared to high slopes are counted. For example, in one actual embodiment of the defibrillator 10, the number of portions having a slope less than about $\frac{1}{16}$ of the highest slopes are counted as a value Histo1, while the number of portions having a slope less than about $\frac{1}{8}$ of the highest slopes are counted as a value Histo2. If either Histo1 or Histo2 exceed specified limits, the defibrillator 10 considers the ECG as having a high baseline content.

Average amplitude, as the name suggests, is a measure of the average amplitude of the ECG data. The average amplitude may be calculated by summing absolute values of the data points in the segment of ECG data, and dividing the result by the number of data points. Alternatively, intermediate average amplitude values may be calculated for each of the smaller portions of the ECG segment (defined above for calculating baseline content) with an overall average amplitude calculated from the intermediate average amplitude values. The average amplitude measure is preferably scaled to a predefined range of values.

Average frequency, as the name suggests, is a measure of the average frequency of the ECG. The average frequency may be calculated by dividing a weighted summation of the derivative of the ECG data by a weighted summation of the absolute values of the ECG data. The average frequency measure is also preferably scaled to a predefined range of values.

R-wave count is a measure of the number of QRS complexes that appear to be present in the segment of ECG data. The positive and negative-sloped portions of the ECG segment (previously defined with respect to calculating baseline content) may be evaluated separately to produce two R-wave counts, namely, PRNUM (for positive-sloped portions) and NRNUM (for negative-sloped portions). An ECG portion is designated as indicating a QRS complex (thus incrementing the R-wave count) when the average slope of the portion exceeds a predefined limit.

ECG rate is a measure that estimates the rate of heart beats occurring in the ECG data. Not all of the portions of the ECG data previously defined with respect to calculation of baseline content need to be used to calculate the ECG rate. For instance, the ECG rate may be calculated using only the portions of the ECG data having a peak-to-peak amplitude and peak slope that exceed predetermined minimum peak-to-peak amplitude and slope thresholds. One actual embodiment of the defibrillator 10 uses the portions of the ECG data that are in the upper 75% of peak-to-peak amplitude and in the upper 67% of peak slope to calculate ECG rate. In addition, the positive and negative sloped portions may be analyzed separately, producing two estimates of the ECG rate. In that regard, the lower of the two estimates is preferably used as the ECG rate measure.

Returning to FIG. 4, the ECG analysis process 100 uses one or more of the ECG measures calculated in block 104 to classify the ECG as "shockable" or "non-shockable" in a block 106 (i.e., to determine whether the patient should be treated by a defibrillation pulse). In an actual embodiment of the defibrillator 10, the five ECG measures discussed above are analyzed in the following manner to classify the patient's ECG.

With regard to baseline content, if there is a high percentage of low-slope ECG data (i.e., flat baseline), the patient's ECG is classified as non-shockable. In that regard, both of the values Histo1 and Histo2 may be evaluated with respect to certain predetermined limits. If either Histo1 or Histo2 exceed the predetermined limits, the defibrillator 10 decides that there is enough baseline content in the ECG data to justify a no-shock classification.

With regard to average amplitude, the defibrillator 10 compares the average amplitude measure to a threshold value to determine if the ECG should be classified as shockable or non-shockable. One actual embodiment of the defibrillator 10 classifies the ECG as non-shockable if the average amplitude measure is below a specified threshold representing approximately 62 microvolts, peak-to-peak. A cardiac rhythm with an average amplitude that exceeds the specified threshold is more likely to be low-amplitude ventricular fibrillation or other rhythm type than cardiac asystole.

The average frequency measure may be also compared to a threshold value to determine whether the ECG should be classified as non-shockable. One actual embodiment of the defibrillator 10 compares the average frequency measure to a specified threshold representing approximately 12 Hz. If the average frequency measure exceeds the specified threshold, the defibrillator 10 concludes there is excessive higher frequency noise in the data that prevents the defibrillator 10 from properly analyzing the ECG. In that case, the ECG is classified as non-shockable.

With regard to R-wave count, if the number of R-waves exceeds a predefined threshold, the ECG segment is classified as non-shockable. If the positive and negative-sloped portions are counted separately to produce the values PRNUM and NRNUM as earlier described, two separate R-wave thresholds PRLIM and NRLIM may be used. Adjustments to the predefined R-wave threshold(s) may be made to take into account ECG portions designated as R-waves that are too close to each other in time to truly be R-waves. Adjustments to the R-wave threshold(s) may also be made if a low degree of similarity exists between the ECG portions designated as R-waves. In an actual embodiment of the defibrillator 10, the R-wave thresholds PRLIM and NRLIM are initially set to about one-half of the calculated ECG rate measure, plus or minus a factor determined from an estimate of the noise in the ECG data.

As for the ECG rate measure, the ECG rate is compared to a minimum and maximum limit. If the ECG rate is below the minimum limit, or above the maximum limit, the ECG segment is classified as non-shockable.

The ECG segment is not classified as non-shockable by any of the above procedures, the ECG is classified as shockable. Additional description of suitable methods for classifying an ECG as shockable or non-shockable is provided in U.S. Pat. Nos. 4,610,254 and 4,619,265, which are assigned to the assignee of the present invention and incorporated herein by reference.

While the above five ECG measures are calculated in one actual embodiment of the present invention, other ECG measures may be calculated as determined to be pertinent to the classification of the cardiac rhythm indicated in the ECG. Such ECG measures include, for example, the detection and characterization of the P-wave and T-wave morphology as performed in 12-lead ECG analysis. A count of zero crossings per second, the median frequency of the ECG, and a measure of QRS duration may also be used. Other possible measures include measures derived from decomposition of the ECG signals in terms of a Karhonen-Loeve transformation or other time-frequency transformation to parameterize the morphology of the ECG. These measures are useful not only to differentiate shockable from non-shockable rhythms, but also to classify an ECG according to cardiac rhythm as discussed below.

Returning again to FIG. 4, once the ECG is classified as shockable or non-shockable in block 106, the ECG analysis process 100 classifies the ECG according to rhythm type in a block 108. In one actual embodiment of the defibrillator 10, the patient's ECG is classified into one of seven rhythm types, namely, ventricular tachycardia, ventricular fibrillation, fine ventricular fibrillation, noisy asystole, asystole, organized and other non-shockable rhythms, and non-shockable tachycardia. In particular, this embodiment of the defibrillator 10 uses a binary classification and regression tree to classify the ECG data into one of the above rhythm types. FIGS. 5–13 illustrate a binary classification and regression tree generated by providing a population of previously-obtained ECG segments having a known cardiac rhythm to a software application named CART by Salford Systems of San Diego, Calif. The CART software application uses the previously-obtained ECG data and known classifications to statistically produce decision rules that systematically predict the rhythm classification of an ECG segment of unknown rhythm type.

The series of binary decision rules used in the classification and regression tree shown in FIGS. 5–13 classifies a segment of ECG data into a class representing one of the different rhythm types identified above. It should be understood that FIGS. 5–13 illustrate only one implementation of a classification and regression tree that may be used to classify a patient's ECG data according to rhythm type. This classification and regression tree in particular uses the five ECG measures calculated in block 104 (FIG. 4), along with the shock/no-shock decision produced in block 106. Of course, other embodiments of the invention may use classification and regression trees derived in a different manner. For additional information on techniques for preparing a classification and regression tree, see *Classification and Regression Trees*, by L. Breiman, J. Friedman, R. Olshen, and C. Stone, Wadsworth International Group, Belmont, Calif. (1984). See also *Linear Machine Decision Trees*, by P. Utgoff and C. Bradley, COINS Technical Report 91-10, Univ. of Massachusetts, Amhurst, Mass. (January 1991), and *Tree Structured Classification Via Generalized Discriminant Analysis*, by W. Loh and N. Vanichsetakul, J. of the ASA, v. 83, n. 403, pp. 715–728 (September 1988).

In FIGS. 5–13, the seven different rhythm types discussed above are identified by class numbers as shown in Table 1. The rhythm types are ordered as shown in Table 1 so that rhythms that are similarly treated are grouped in adjoining classes.

TABLE 1

| | |
|---|---|
| Class 1 | Ventricular tachycardia |
| Class 2 | Ventricular fibrillation |
| Class 3 | Fine ventricular fibrillation |
| Class 4 | Noisy asystole |
| Class 5 | Asystole |
| Class 6 | Other non-shockable rhythms |
| Class 7 | Non-shockable tachycardia |

At each of the nodes N1, N2, N3, . . . N57 in the classification and regression tree shown in FIGS. 5–13, a linear decision rule is applied to determine whether the segment of ECG data under current evaluation should be classified toward the next lower node on the left or the next lower node on the right. For example, in FIG. 5, a linear decision rule applied at node N1 determines whether the ECG segment under evaluation should be classified toward the lower left node N2 or to the lower right node N49. At either of nodes N2 or N49, another linear decision rule is applied to the ECG segment to again determine whether the ECG should be classified toward the lower left node or the lower right node (e.g., for node N2, toward the lower left node N3 or the lower right node N16). This binary partitioning continues until the ECG segment is classified into one of the classifications Class 1–Class 7 referenced in Table 1. For instance, in FIG. 5, if the linear decision rule at node N50 determines that the ECG segment should be classified toward the lower right node, the ECG segment is classified as Class 2 (i.e., ventricular fibrillation). Table 2 below sets forth the linear decision rules used in one embodiment of the defibrillator 10 at each of the nodes illustrated in FIGS. 5–13.

TABLE 2

| Node | Decision Rule | Node (or Class) if True | Node (or Class) if False |
|---|---|---|---|
| N1 | −0.731(AVEFREQ)−0.683(HISTO1) ≦ −93.906 | N2 | N49 |
| N2 | AVEAMP ≦ 48.5 | N3 | N16 |
| N3 | −0.995(AVEAMP)−0.104(HISTO2) ≦ −52.395 | N4 | N8 |
| N4 | HISTO2 ≦ 252.5 | N5 | N7 |
| N5 | AVEFREQ ≦ 52.5 | Class 7 | N6 |
| N6 | PRDIF ≦ −1.5 | Class 4 | Class 3 |
| N7 | AVEFREQ ≦ 87.5 | Class 6 | Class 4 |
| N8 | AVEAMP ≦ 19.5 | N9 | N11 |

TABLE 2-continued

| Node | Decision Rule | Node (or Class) if True | Node (or Class) if False |
|------|---------------|-------------------------|--------------------------|
| N9 | −0.993(AVEAMP)+0.118(HISTO1) ≤ −3.495 | N10 | Class 5 |
| N10 | −0.625(AVEAMP)−0.781(AVEFREQ) ≤ −64.89 | Class 5 | Class 6 |
| N11 | AVEFREQ ≤ 60.5 | N12 | N13 |
| N12 | HISTO2 ≤ 135.5 | Class 3 | Class 6 |
| N13 | −0.946(AVEAMP)−0.323(AVEFREQ) ≤ −53.833 | N14 | Class 5 |
| N14 | AVEAMP ≤ 27.5 | Class 3 | N15 |
| N15 | AVEFREQ ≤ 64.5 | Class 3 | Class 4 |
| N16 | NRDIF ≤ −2.5 | N17 | N26 |
| N17 | 0.004(HISTO1)−1.0(RATE) ≤ −2.555 | N18 | N23 |
| N18 | −0.035(AVEAMP)−0.999(AVEFREQ) ≤ −45.501 | N19 | N21 |
| N19 | 0.241(AVEFREQ)−0.046(HISTO2)−0.969(PRDIF) ≤ 9.424 | Class 7 | N20 |
| N20 | HISTO2 ≤ 130.5 | Class 3 | Class 4 |
| N21 | AVEAMP ≤ 68.5 | Class 7 | N22 |
| N22 | HISTO2 ≤ 200 | Class 1 | Class 7 |
| N23 | 0.754629E-04(AVEAMP)−0.242813E-03(AVEFREQ)−0.697096E-05(HISTO1)−1.0(PRDIF) ≤ 2.994 | Class 7 | N24 |
| N24 | −0.026(AVEAMP)+1.0(AVEFREQ) ≤ 32.065 | N25 | Class 7 |
| N25 | AVEAMP ≤ 226.0 | Class 1 | Class 7 |
| N26 | HISTO2 ≤ 148.5 | N27 | N29 |
| N27 | AVEAMP ≤ 109.5 | N28 | Class 7 |
| N28 | HISTO1 ≤ 86.5 | Class 2 | Class 4 |
| N29 | HISTO2 ≤ 300.5 | N30 | N46 |
| N30 | −0.115(AVEAMP)+0.993(HISTO2) ≤ 257.331 | N31 | N41 |
| N31 | AVEAMP ≤ 264.5 | N32 | N36 |
| N32 | −0.405399E-03(AVEAMP)+0.038(RATE)+0.999(NRDIF) ≤ 1.041 | N33 | Class 7 |
| N33 | 0.019(HISTO1)+1.0(NRDIF) ≤ 1.149 | N34 | Class 6 |
| N34 | AVEAMP ≤ 187.5 | N35 | Class 1 |
| N35 | AVEFREQ ≤ 78.5 | Class 6 | Class 3 |
| N36 | −0.083(AVEAMP)−0.997(HISTO2) ≤ −309.206 | N37 | N38 |
| N37 | RATE ≤ 2.5 | Class 4 | Class 2 |
| N38 | 0.318827E-04(HISTO2)+0.038(RATE)−0.999(NRDIF) ≤ −0.84 | Class 6 | N39 |
| N39 | HISTO2 ≤ 273.5 | N40 | Class 2 |
| N40 | HISTO1 ≤ 248.0 | Class 6 | Class 4 |
| N41 | 0.070(AVEFREQ)+0.998(PRDIF) ≤ 4.534 | N42 | N45 |
| N42 | −0.074(AVEAMP)+0.151(HISTO1)−0.986(PRDIF) ≤ 25.481 | Class 3 | N43 |
| N43 | −0.02(AVEAMP)+0.019(AVEFREQ)+1.0(NRDIF) ≤ −2.797 | N44 | Class 6 |
| N44 | RATE ≤ 0.5 | Class 3 | Class 6 |
| N45 | NRDIF ≤ −0.5 | Class 1 | Class 6 |
| N46 | AVEFREQ ≤ 66.5 | Class 1 | N47 |
| N47 | RATE ≤ 1.5 | N48 | Class 1 |
| N48 | AVEAMP ≤ 258.5 | Class 6 | Class 3 |
| N49 | 1.0(SHKADV)−0.908224E-03(AVEAMP) ≤ −0.096 | N50 | N54 |
| N50 | 0.003(AVEAMP)+0.572(RATE)−0.820(PRDIF) ≤ 6.649 | N51 | Class 2 |
| N51 | −0.076(AVEFREQ)+0.997(RATE) ≤ 0.526 | N52 | Class 1 |
| N52 | HISTO2 ≤ 100.0 | Class 2 | N53 |
| N53 | AVEAMP ≤ 113.5 | Class 1 | Class 7 |
| N54 | −0.220(AVEAMP)+0.976(AVEFREQ) ≤ 30.203 | N55 | Class 2 |
| N55 | 0.533(AVEAMP)−0.846(HISTO2) ≤ 5.218 | N56 | Class 2 |
| N56 | HISTO2 ≤ 124.5 | Class 2 | N57 |
| N57 | NRDIF ≤ −3.5 | Class 2 | Class 7 |

In Table 2 above, the values HISTO1 and HISTO2 are calculated as described earlier in determining baseline content. The values AVEAMP, AVEFREQ, and RATE are the average amplitude, average frequency, and ECG rate measures, respectively, also calculated as described earlier. The value SHKADV equals "1" if the ECG was classified as shockable in block 106 (FIG. 4), and "0" if classified as non-shockable. The value PRDIF in Table 2 is a composite number representing the difference between the R-wave count PRNUM and the R-wave threshold PRLIM, and the value NRDIF is a composite number representing the difference between the R-wave count NRNUM and the R-wave threshold NRLIM.

Returning to FIG. 4, once the ECG segment is classified as to rhythm type in block 108, the ECG analysis process 100 records the ECG classification (i.e., the classification of the ECG as shockable or non-shockable, and the classification of the ECG as a particular rhythm type) in a block 110. In that regard, the ECG classification is preferably recorded in memory 60 (FIG. 2).

Returning now to FIG. 3, after completing the ECG analysis in block 72, the ECG evaluation process 70*a* determines in a decision block 74 whether the patient's ECG was classified as a shockable cardiac rhythm. If so, the defibrillator 10 prompts "Shock Advised" in a block 76 to advise the operator of the defibrillator 10 that a defibrillation pulse is recommended. In a block 78, the defibrillator 10 proceeds to charge its defibrillation capacitors. When the defibrillation capacitors are charged, the defibrillator 10 informs the operator that the defibrillation pulse is ready for delivery. In a block 80, the charge stored in the defibrillation capacitors is delivered to the patient in a form of a defibrillation pulse, preferably when the operator of the defibrillator 10 initiates the appropriate user input.

If, in decision block 74, the patient's cardiac rhythm was found to be classified as a non-shockable rhythm, the defibrillator 10 determines in a decision block 82 whether the ECG analysis performed in block 72 also classified the patient's cardiac rhythm as asystole. With regard to the embodiment of the invention described in reference to Table 1, both classifications "noisy asystole" and "asystole" are treated by the ECG evaluation process 70 as a classification of "asystole" (in essence, making a super class of "asystole" for treatment purposes that includes both rhythm classes of asystole and noisy asystole). In the version 70a of the ECG evaluation process 70, the defibrillator 10 prompts the operator of the defibrillator in a block 84 with the message "Asystole; No Shock Advised" if the patient's ECG was classified as asystole.

If, in decision block 82, the defibrillator 10 determines that the patient's cardiac rhythm was classified as non-asystole (i.e., by virtue of being classified in a rhythm class other than asystole and noisy asystole), the defibrillator 10 does not report "Asystole" but instead in a block 86 prompts the operator of the defibrillator with the message "No Shock Advised." Knowing whether the patient is in an asystolic condition will assist the operator of the defibrillator 10 in determining whether to continue providing therapy (i.e., in accordance with the medical protocol established for such circumstances).

Figure 14:
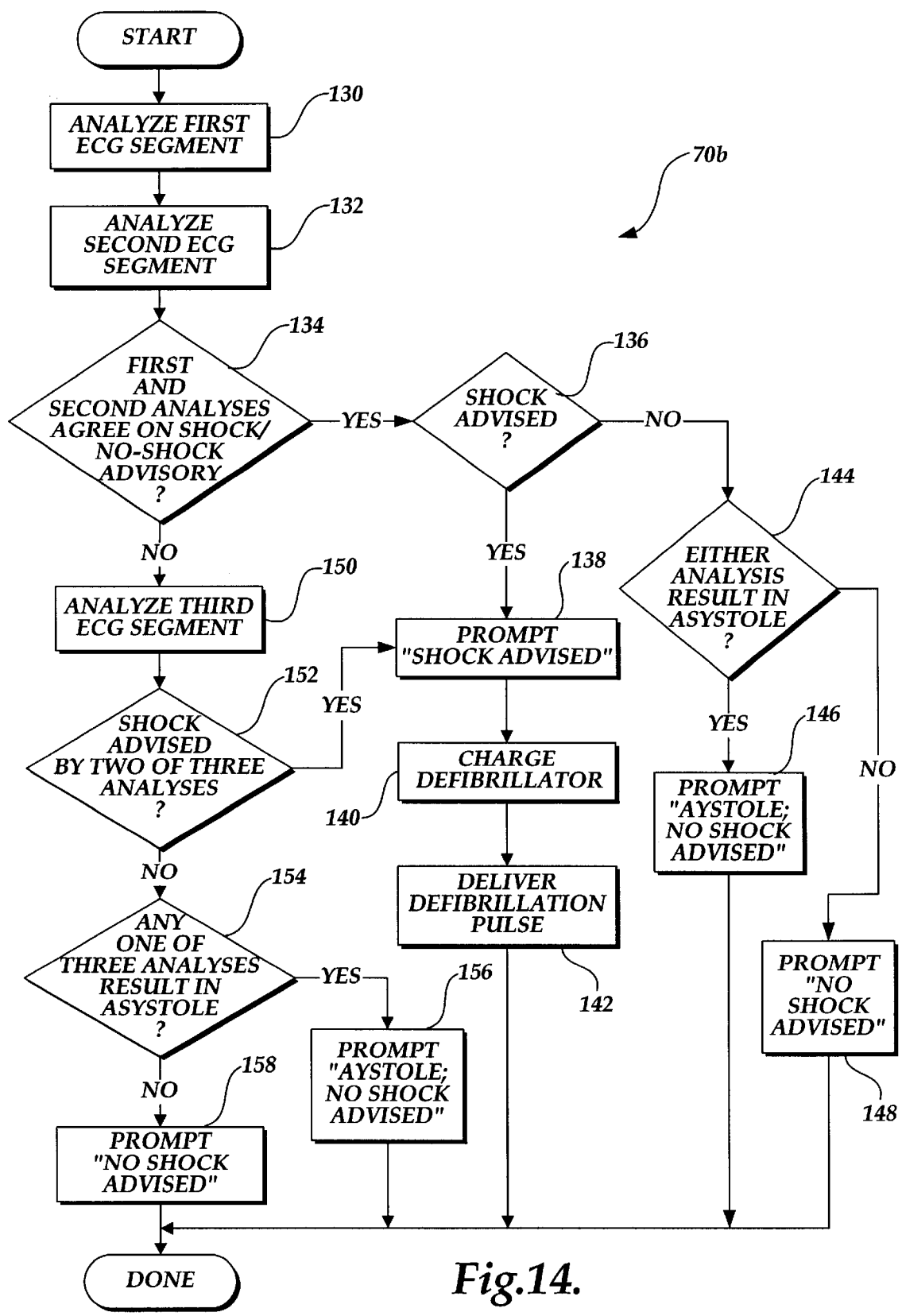
FIG. 14 is a flow diagram of another version of the ECG evaluation process used by the defibrillator shown in FIG. 1 wherein multiple segments of ECG data are evaluated and a consensus decision is obtained prior to reporting a detection of cardiac asystole.

FIG. 14 illustrates another version 70b of the ECG evaluation process 70. In this version 70b, the defibrillator 10 analyzes multiple segments of ECG data to obtain a consensus decision as to (1) whether a defibrillation shock should be provided, and (2) whether a non-shockable cardiac rhythm is asystole. More specifically, the ECG evaluation process 70b begins in a block 130 by analyzing a first segment of ECG data in a manner as described in reference to FIG. 4. Next, in a block 132, the defibrillator 10 analyzes a second segment of ECG data, again in a manner as described in reference to FIG. 4.

After analyzing the first and second ECG segments, the defibrillator 10 determines in a decision block 134 whether both the first and second ECG analyses agree on whether a shockable or non-shockable rhythm was detected. If the first and second analyses agree in that regard, the defibrillator 10 then determines in a decision block 136 whether the agreed result is that a shockable rhythm was detected. If so, the defibrillator 10 prompts the operator of the defibrillator in a block 138 with the message "Shock Advised." The defibrillator 10 then charges the defibrillation capacitors in a block 140 and delivers a defibrillation pulse to the patient in a block 142, in a manner as discussed earlier in reference to blocks 76, 78, and 80 in FIG. 3.

If, in decision block 136, the agreed result of the first and second ECG analyses is that a non-shockable rhythm was detected, the defibrillator 10 then determines in a decision block 144 whether either of the two ECG analyses resulted in a detection of asystole. If the patient's cardiac rhythm was classified as asystole in either ECG analysis, the defibrillator 10 prompts the operator in a block 146 with the message "Asystole; No Shock Advised". If neither the first or second ECG analysis classified the patient's cardiac rhythm as asystole (though both analyses agreed that the rhythm was non-shockable), the operator is prompted in a block 148 with the message "No Shock Advised."

Returning to decision block 134, if the first and second ECG analyses do not agree on whether a shock is advised (i.e., one ECG analysis classified the patient's cardiac rhythm as a shockable rhythm and the other ECG analysis classified the cardiac rhythm as a non-shockable rhythm), the defibrillator 10 analyzes a third ECG segment in a block 150 in a manner as described in reference to FIG. 4. The defibrillator 10 then evaluates the results of the three ECG analyses in a block 152 to determine whether two of the three analyses agree that delivery of a shock is advised. If the consensus decision is that a shock is advised (i.e., two of the three ECG segments were classified as shockable), the defibrillator 10 proceeds to prepare and deliver a defibrillation pulse in blocks 138, 140, and 142 as discussed above.

Otherwise, the defibrillator 10 proceeds to a decision block 154 where it determines whether any one of the three ECG analyses classified the patient's cardiac rhythm as asystole. If any one of the ECG analyses resulted in detection of asystole, the defibrillator 10 prompts the operator in a block 156 with the message "Asystole; No Shock Advised." If not, the defibrillator 10 prompts the operator in a block 158 with the message "No Shock Advised."

Figure 15:
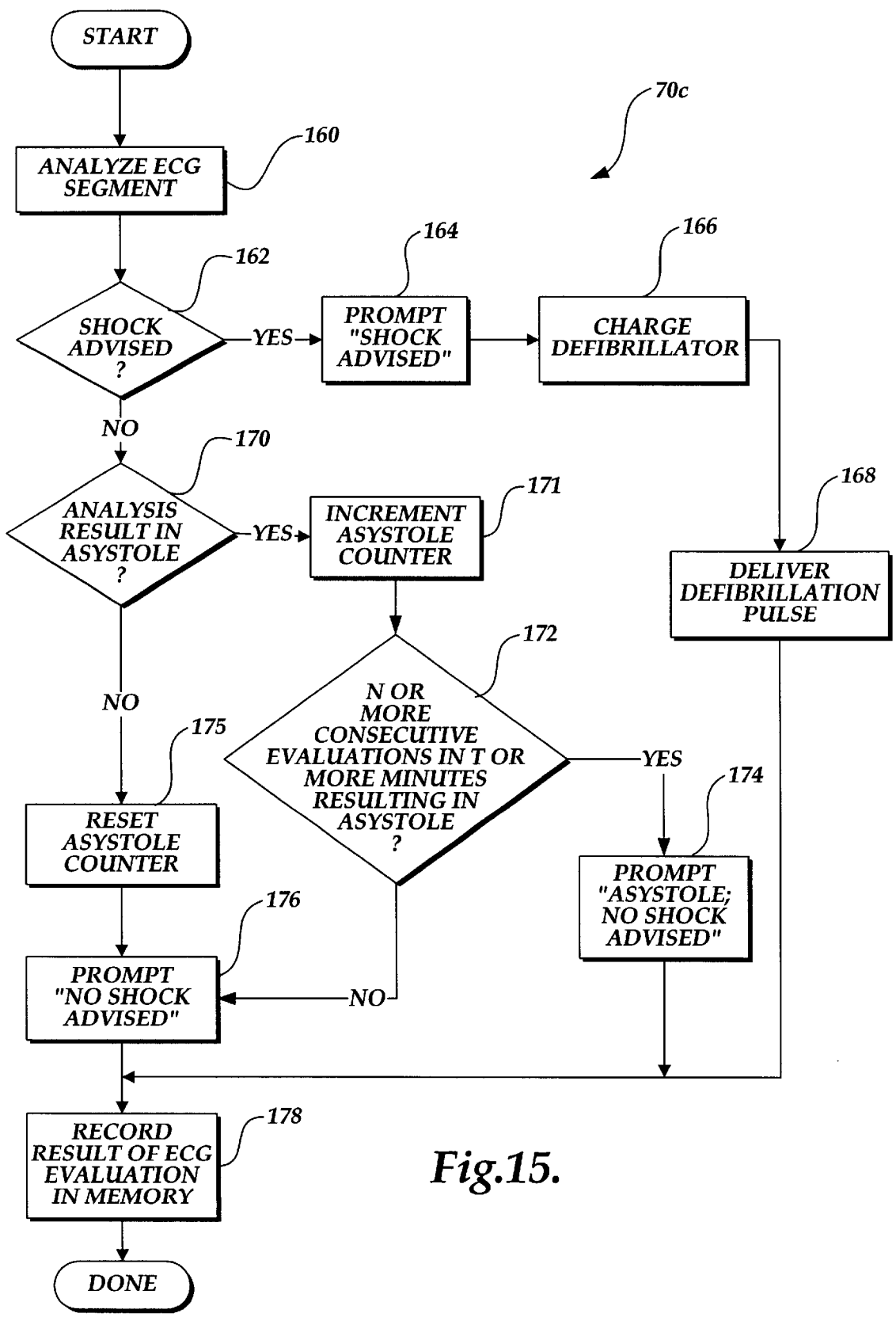
FIG. 15 is a flow diagram of yet another version of the ECG evaluation process used by the defibrillator shown in FIG. 1 wherein consecutive evaluations resulting in asystole over a period of time are required prior to reporting a detection of cardiac asystole.

FIG. 15 illustrates yet another version 70c of the ECG evaluation process 70. In this version 70c, the defibrillator 10 requires a predetermined number of consecutive ECG evaluations over a prescribed period of time resulting in an asystole classification prior to reporting "Asystole" to the operator of the defibrillator. In essence, the ECG evaluation process 70c only reports cardiac asystole when the asystole classification is persistent. A report of persistent asystole is particularly useful for triage and may be used as grounds for termination of resuscitation efforts in the field, or as grounds for a decision to continue CPR but not transport the patient immediately to a hospital.

The ECG evaluation process 70c begins in a block 160 by analyzing a segment of ECG data in a manner as described earlier in reference to FIG. 4. Although the ECG evaluation process 70c is shown in FIG. 15 as analyzing only one segment of ECG data, it should be understood that, alternatively, multiple segments of ECG data may be analyzed in the manner shown in FIG. 14.

In a decision block 162, the defibrillator 10 evaluates the result of the ECG analysis of block 160 and determines whether a defibrillation shock is advised (i.e., whether the patient's cardiac rhythm was classified as a shockable rhythm). If a defibrillation shock is advised, the defibrillator 10 prompts the operator with the message "Shock Advised" in a block 164, prepares a defibrillation charge in a block 166, and delivers a defibrillation pulse in a block 168, in a manner as described earlier in reference to blocks 76, 78, and 80 in FIG. 3.

If, in decision block 162, the defibrillator 10 determines that a defibrillation shock is not advised (i.e., that the patient's cardiac rhythm was classified as non-shockable), the defibrillator 10 determines in a decision block 170 whether the ECG analysis resulted in an asystole classification. If the patient's ECG was classified as asystole, the defibrillator 10 increments a counter that counts the number of consecutive ECG evaluations resulting in asystole. The asystole counter is preferably maintained in the history of ECG evaluation results 63 stored in memory 60 (FIG. 2).

In a decision block 172, the defibrillator 10 reviews the patient's history of ECG evaluation results 63 to determine whether "N" or more consecutive ECG evaluations resulting in an asystole classification have been performed on the patient and whether a period of time "T" has transpired during which all ECG evaluations that were performed resulted in an asystole classification. In one actual embodiment of the defibrillator 10, the time T is selected from a range of 4 to 60 minutes and the number of consecutive asystole results N is defined as 1+T/2. For a time period T equaling four minutes, the number N would be 3. Thus, in this embodiment of the defibrillator 10, a minimum of three consecutive analyses in at least four minutes resulting in a classification of asystole (e.g., as indicated by the asystole counter) would be required before the defibrillator 10 would report the detection of cardiac asystole to the operator.

If the required number of consecutive asystole results N is met and at least the required time period T has transpired, the defibrillator 10 prompts the operator in a block 174 with the message "Asystole; No Shock Advised." Otherwise, the defibrillator 10 does not report the detection of asystole but prompts only "No Shock Advised" in a block 176.

If in decision block 170, the defibrillator 10 determines that cardiac asystole was not detected in the ECG analysis in block 160, the defibrillator 10 resets the asystole counter in a block 175 and reports "No Shock Advised" in block 176. In a block 178, the result of the ECG evaluation process 70c is added to the patient's history of ECG evaluation results 63 stored in memory 60.

The value T referenced above is preferably configurable in the defibrillator 10 when the defibrillator is in a service mode of operation. Medical directors may select and implement an appropriate value for T to control when cardiac asystole is reported to caregivers under their jurisdiction. For instance, a medical director for an airline may want T to be five minutes, giving a patient on an airplane that long to develop a beating heart. If cardiac asystole persists for longer than five minutes, further efforts to resuscitate are likely futile and the airline may decide to not divert the airplane to obtain fastest medical assistance based on the report from the defibrillator 10.

The aspects of the invention shown in the versions 70a, 70b, and 70c of the ECG evaluation process 70 may be used separately or in combination with one another. For example, FIGS. 16A and 16B depict another version 70d of the ECG evaluation process 70 wherein the defibrillator 10 obtains a consensus decision from analyzing multiple segments of ECG data (e.g., as used in version 70b shown in FIG. 14) and requires N consecutive asystole results over at least time T (e.g., as used in version 70c shown in FIG. 15) prior to reporting the detection of cardiac asystole.

The ECG evaluation process 70d also includes another aspect of the invention wherein the defibrillator 10 determines whether a defibrillation pulse was previously delivered to the patient in a specified time period "X" prior to the current ECG evaluation. Since defibrillation pulses are commonly followed by a period of asystole, an asystolic condition detected within time X following delivery of a defibrillation pulse is not reported to the operator of the defibrillator. Rather, the asystole detection is recorded in the history of ECG evaluation results 63 and if asystole continues to be detected in a subsequent evaluation performed outside the period of time X, the message "Asystole" is reported to the operator of the defibrillator. The time value X may be set by a medical director when the defibrillator 10 is in a service mode of operation.

Figure 16A:
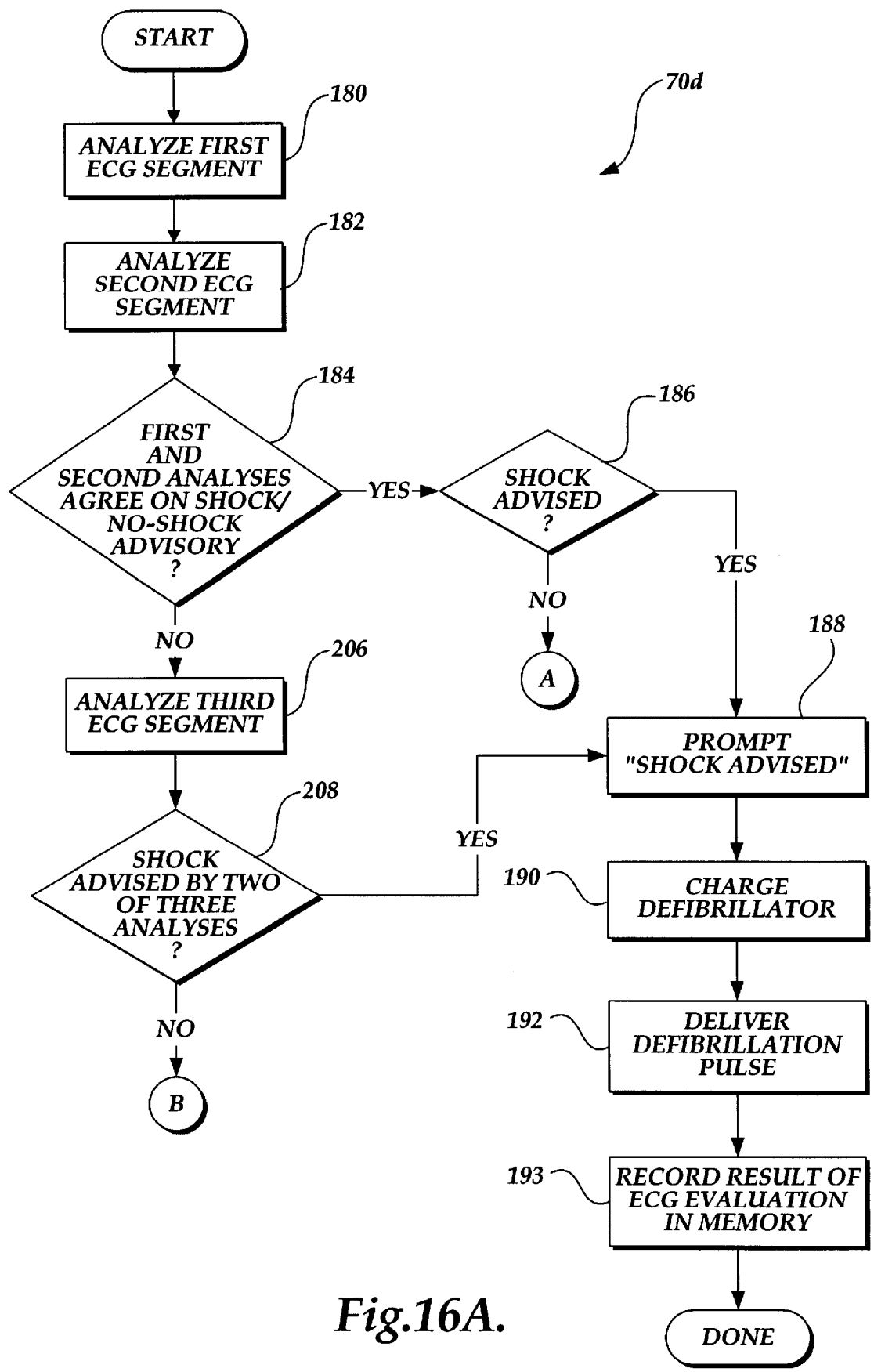
FIGS. 16A and 16B comprise a flow diagram of still another version of the ECG evaluation process used by the defibrillator shown in FIG. 1 that evaluates multiple segments of ECG data (e.g., as depicted in FIG. 14) and requires a history of consecutive ECG evaluations resulting in asystole (e.g., as depicted in FIG. 15) and a determination that a defibrillation pulse has not been previously delivered in a specified time frame, prior to reporting a detection of cardiac asystole.

The ECG evaluation process 70d begins in FIG. 16A by analyzing a first and second segment of ECG data in blocks 180 and 182, respectively. If, in decision block 184, the results of the first and second ECG analyses agree on whether a defibrillation shock should be provided, and if in decision block 186 the results of the first and second ECG analyses agree that a shock is advised, the defibrillator 10 prompts the operator with the message "Shock Advised" in a block 188. The defibrillator 10 then charges the defibrillation capacitors in a block 190 and delivers a defibrillation pulse to the patient in a block 192, in a manner as described earlier in reference to blocks 76, 78, and 80 in FIG. 3. In a block 193, the defibrillator 10 also records the result of the ECG evaluation process 70d (e.g., that a defibrillation shock was advised and delivered) in a history of ECG evaluation results 63 stored in memory 60.

Figure 16B:
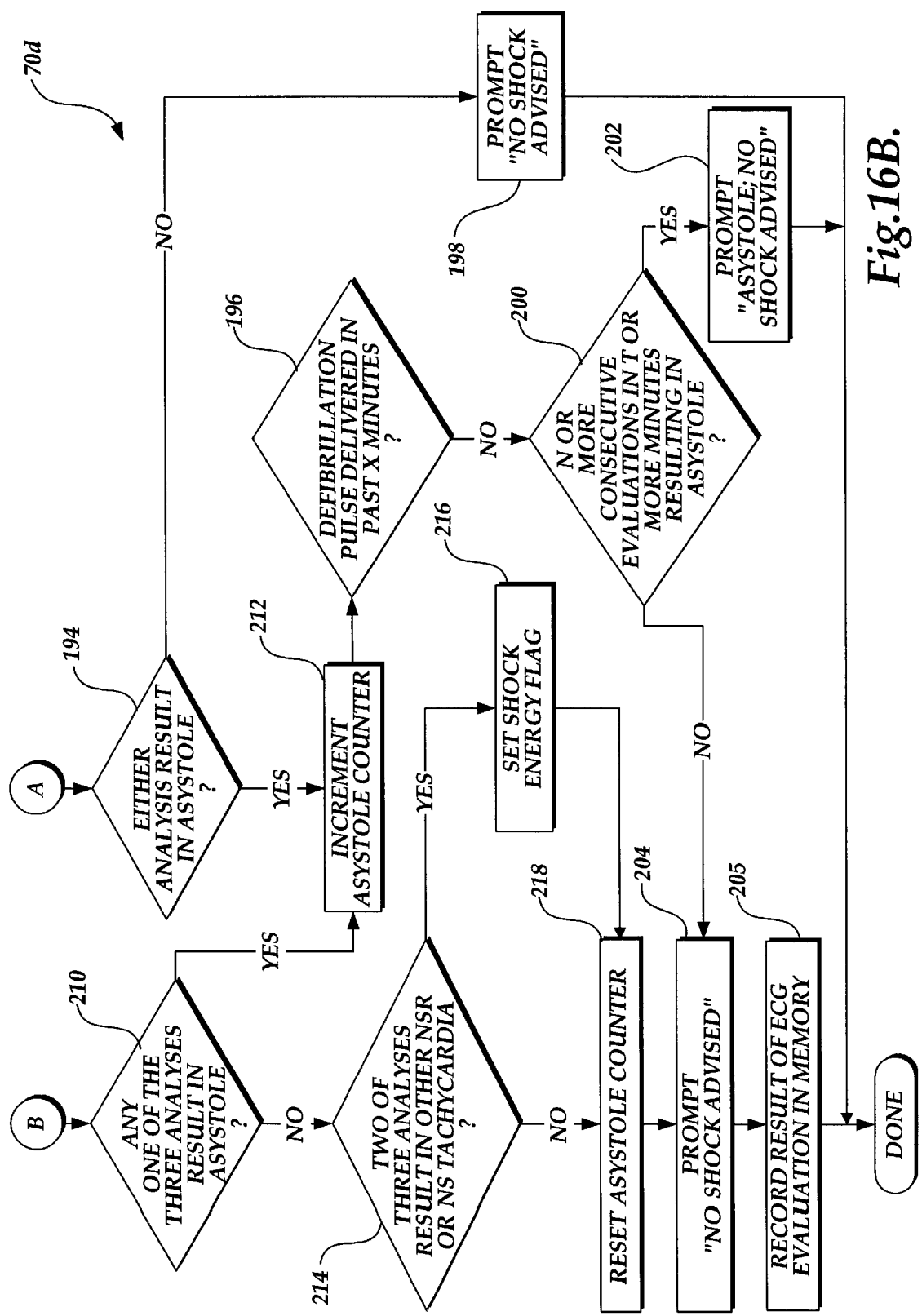

If, in decision block 186, the first and second ECG analyses agree that a shock is not advised (i.e., both ECG segments were classified as non-shockable), the ECG evaluation process 70d is continued at a point A in FIG. 16B where, in a decision block 194, the defibrillator 10 determines whether either of the two ECG analyses classified the patient's cardiac rhythm as asystole. If so, the defibrillator 10 increments an asystole counter in a block 212 that counts the number of ECG evaluations resulting in asystole. As noted earlier, the asystole counter is preferably maintained in the history of ECG evaluation results 63.

The defibrillator 10 then determines in a decision block 196 whether a defibrillation pulse had been previously delivered to the patient in a specified time period X prior to the current ECG evaluation. For example, if the time period X was set to one minute, and a detection of asystole was determined within one minute after delivery of a defibrillation shock, the defibrillator 10 would not report that the patient is in an asystolic condition but instead only prompt "No Shock Advised," as indicated in a block 198. The detection of asystole would, however, be recorded in the patient's history of ECG evaluation results in a block 205.

Returning to decision block 196, if a defibrillation pulse was not previously delivered to the patient in the specified time period X, the defibrillator 10 proceeds to decision block 200 to determine whether the detected asystole is one of N or more consecutive asystole results obtained in T or more time. If so, the defibrillator 10 prompts the operator of the defibrillator in a block 202 with a message "Asystole; No Shock Advised." Otherwise, the defibrillator 10 only prompts "No Shock Advised" in a block 204. In either event, after prompting the operator with a message in block 202 or block 204, the result of the ECG evaluation process 70d is recorded in the patient's history of ECG evaluation results stored in memory 60, as indicated in block 205.

Returning to decision block 184 in FIG. 16A, if the two ECG analyses performed in blocks 180 and 182 did not agree on whether the patient's cardiac rhythm was shockable or non-shockable, the defibrillator 10 proceeds to analyze a third segment of ECG data in a block 206 in a manner as described earlier in reference to FIG. 4. If, in a decision block 208, two of the three ECG analyses agree that the patient's cardiac rhythm is shockable, the defibrillator 10 proceeds to prepare and deliver a defibrillation pulse in blocks 188, 190, and 192, as described above. The defibrillator 10 also records the result of the ECG evaluation process 70d in the patient's history of evaluation results 63 stored in memory 60, as indicated in block 193.

If two of the three ECG analyses agree that the patient's cardiac rhythm is non-shockable, the ECG evaluation process 70d continues from decision block 208 to a decision block 210 at point B in FIG. 16B. In decision block 210, the defibrillator 10 determines whether any one of the three ECG analyses classified the non-shockable rhythm as asystole. If so, the defibrillator 10 increments the asystole counter in block 212. The defibrillator 10 then determines in decision block 196 whether a defibrillation pulse was delivered in a specified time period X prior to the current ECG evaluation. The procedure following the determination in decision block 196 proceeds as earlier described.

If, in decision block 210, the defibrillator 10 determines that none of the three ECG analyses classified the patient's ECG as asystole, the defibrillator 10 determines in a decision block 214 whether two of the three ECG analyses resulted in a classification of "other non-shockable rhythm" or "non-shockable tachycardia" (e.g., as referenced earlier in Table 1). A classification in these two classes of cardiac rhythm indicates the possible presence of cardiac electrical activity that could be associated with perfusion. In accordance with requirements set forth by the International Liaison Committee on Resuscitation (ILCOR) in connection with such circumstances, the defibrillator 10 sets a flag variable in a block 216 that causes the next defibrillation pulse to be delivered to the patient (if another ECG evaluation results in a shockable rhythm) to convey the same amount of energy as the last defibrillation pulse (if there was one) delivered to the patient. The defibrillator 10 also resets the asystole counter to zero in block 218 and prompts "No Shock Advised" in block 204 to the operator of the defibrillator. The result of the ECG evaluation is recorded in memory 60 in block 205.

If, in decision block 214, two of the three ECG analyses did not result in "other non-shockable rhythm" or "non-shockable tachycardia," two of the three ECG analyses must have resulted in a classification of "ventricular fibrillation," "ventricular tachycardia," or "fine ventricular fibrillation" (i.e., the remaining three classes shown in Table 1). A classification in one of these three rhythm classes at this point is unusual because the ECG was previously declared to be non-shockable. Nevertheless, these rhythm classes are generally not associated with perfusion. As such, for treatment purposes, classifications in these rhythm classes at this point may be grouped together in a super class identified for non-shockable basic life support. The currently preferred treatment in this circumstance is to continue application of basic life support and not set the shock energy flag (as provided in block 216). Proceeding to block 218, the asystole counter is reset to zero. After the operator is prompted with the message "No Shock Advised" in block 204, the result of the ECG evaluation process 70d is recorded in block 205 in the patient's history of ECG evaluation results.

In an actual embodiment of the defibrillator 10, evaluating the outcome of multiple ECG analyses is performed by first assigning predetermined values to the possible rhythm classifications (e.g., "1" for ventricular tachycardia, "2" for ventricular fibrillation, etc.). The values representing the classification results of each of the ECG analyses in blocks 180, 182, and 206, are weighted and combined to produce a composite index value. The composite index value is applied to a predetermined look-up table to determine whether any one of the ECG evaluations resulted in asystole, whether any two of the ECG evaluations resulted in "other non-shockable rhythm" or "non-shockable tachycardia," etc. The look-up table is prepared so that a combination of ECG analyses used as an index will map to a value in the look-up table representative of the appropriate outcome for the ECG evaluation. For example, with respect to decision block 214, a composite index value calculated as a function of three ECG analyses in which two of the three analyses resulted in "other non-shockable rhythm" would be applied to the look-up table and the look-up table would return a value indicating that the consensus decision for decision block 214 is an overall classification of "other non-shockable rhythm."

Figure 17:
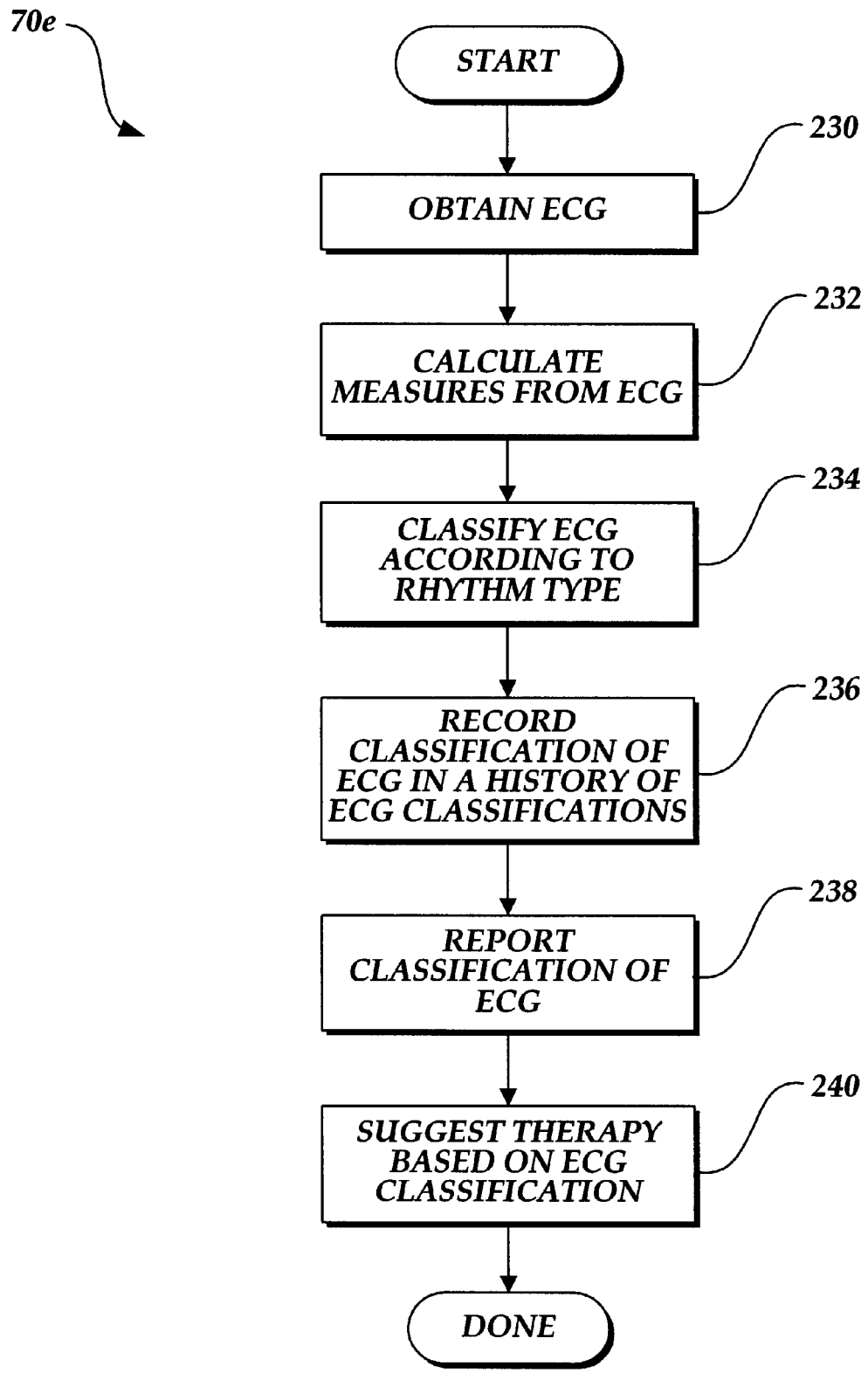
FIG. 17 is a flow diagram of still another version of the ECG evaluation process used by the defibrillator shown in FIG. 1 wherein a single classifier is used to classify the ECG into a rhythm class and therapy is suggested based on the rhythm class into which the ECG is classified.

In the versions 70a, 70b, 70c, and 70d of the ECG evaluation process 70 discussed above, the ECG measures derived from the ECG data are evaluated to first classify the ECG as shockable or non-shockable, and if non-shockable, then classify the ECG as asystole or some other (non-asystole) cardiac rhythm. In another implementation of the present invention, the ECG evaluation process 70 may directly classify the ECG as shockable, asystole, or non-asystole in a single classifier. In that regard, FIG. 17 illustrates a version 70e of the ECG evaluation process 70 in which the ECG measures are used to directly classify the ECG into one of several rhythm classes. In blocks 230 and 232, respectively, a segment of ECG data is obtained from a patient and one or more ECG measures are calculated from the ECG data (e.g., in a manner as described in reference to blocks 102 and 104 in FIG. 4). In a block 234, the segment of ECG data is classified according to one of several types of cardiac rhythms (e.g., in a manner as described in reference to block 108 in FIG. 4). If the ECG is classified as ventricular tachycardia, ventricular fibrillation, or fine ventricular fibrillation, for example, the ECG is classified as "shockable." If the ECG is classified as asystole or noisy asystole, the ECG is classified as "asystole." Lastly if the ECG is classified as non-shockable tachycardia or other non-shockable rhythm, the ECG is classified as "non-asystole."

In a block 236, the defibrillator 10 records the classification of the ECG in a history of ECG classifications 63 stored in memory (60) (FIG. 2). If the history of ECG classifications 63 indicates that a predetermined number of consecutive ECG evaluations resulted in a classification of asystole in at least a predetermined period of time, the defibrillator 10 prompts a message in a block 238 reporting cardiac asystole. The defibrillator 10 may also report in block 238 the rhythm type of the ECG (if not asystole) as classified in block 234. Alternatively, the defibrillator 10 may simply report the shockable, asystole, or non-asystole classification. In a block 240, the defibrillator 10 automatically suggests a procedure to undertake, in this case a therapy, based on the ECG classification. For example, defibrillation therapy may be suggested for ECGs classified as "shockable." The procedure suggested by the defibrillator 10 may also be an instruction providing guidance for prioritizing the delivery of care to the patient.

Classification of the patient's ECG into multiple rhythm classes as discussed herein may be usedl for more than reporting the detection of cardiac asystole in a patient. Using the techniques described herein, a multitherapy device could classify a patient's ECG according to a rhythm class and guide a caregiver to follow a more complex protocol in treating the patient. For instance, the device could advise immediate application of a defibrillation pulse for large-amplitude ventricular fibrillation, advise application of CPR for a minute or two prior to defibrillation for medium- or small-amplitude ventricular fibrillation, use a lower-energy shock synchronized to a QRS complex in the ECG to cardiovert ventricular tachycardia, advise CPR for non-shockable tachycardia, and/or advise an injection of epinephrine for asystole. For other non-shockable rhythms, the multitherapy device may provide external pacing to increase the heart rate and increase blood flow to the vital organs. The multitherapy device may be configured to detect greater or fewer classes of cardiac rhythm than the seven rhythm classes discussed herein.

While several versions of the ECG evaluation process 70 have been illustrated and described above, it will be appreciated that other various changes can be made without departing from the scope of the invention. For example, although not shown, the consensus decision aspect of analyzing multiple ECG segments (as shown in FIG. 14) may be included in the version 70c of the ECG evaluation process shown in FIG. 15. Other possible variations include, for example, combining the determination of whether a defibrillation pulse was previously provided (as described in version 70d shown in FIGS. 16A and 16B) with the consensus decision aspect (as used in version 70b shown in FIG. 14). The consensus decision aspect may also employ more than three ECG analyses, with the consensus decision determined by the majority outcome (e.g., three out of five, four out of seven, etc.).

As another alternative, the classification and regression tree illustrated in FIGS. 5–13 and used in block 108 may be replaced with a three-way classifier that directly classifies the ECG as shockable, non-shockable asystole, or non-shockable non-asystole using the ECG measures. The three-way classifier may be derived using known statistical methods, such as a Gaussian or linear/logistic regression model in which the classifier is trained using ECG measures calculated from a population of ECGs exhibiting known cardiac rhythm. The defibrillator 10 may suggest a therapy based on the classification, such as application of a defibrillation pulse, reporting "Asystole," or prompting "No Shock Advised."

Furthermore, while analysis of one or more segments of ECG data is described above for certain exemplary embodiments of the invention, other embodiments of the invention may analyze the patient's ECG signals on a continuous basis to detect and report information on cardiac condition. In that regard, the defibrillator 10 would employ one or more continuous filters that identify particular characteristics in the ECG signals being analyzed, such as frequency and amplitude, or non-linear estimations of noise outside the frequency range of ECG signals. To identify characteristics in the ECG signals over a range of time, selected continuous filters may be configured with a delay element. The continuous filters may be implemented through digital signal processing performed in the processing unit 58 (FIG. 2) or in one or more separate digital or analog processing components (not shown) in signal communication with the processing unit 58. One or more classifiers receiving the output of the continuous filters would classify the ECG signals at one or more instances of time indicating the cardiac condition of the patient and, in accordance with the invention, the classification information would be reported to enable the user of the defibrillator 10 to make meaningful triage and treatment decisions.

It is important to recognize that, as noted earlier, the present invention may be implemented in a device that is not dependent on the availability of defibrillation. A medical support device of this kind would provide, in accordance with the invention, reliable information on a patient's cardiac condition on which first-responding caregivers may make emergency handling and treatment decisions without first requiring the benefit of expert human intervention (i.e., without requiring prior instruction from an attending physician in an emergency room). In the same manner as an automated external defibrillator provides instruction, a medical support device of this kind would prompt messages on a display that provide direction and support to both the patient and the caregivers at the scene. If the medical support device classifies the signal data obtained from the patient according to type of cardiac rhythm, the medical support device may tailor the information given to the first-responding caregivers according to the rhythm class of the signal data.

It is also important to recognize that, as noted earlier, the present invention may use other non-invasive signals indicative of cardiac condition, in conjunction with ECG signals, to detect and report information on cardiac condition for caregivers making triage and patient routing decisions. For instance, a device implementing the present invention may use transthoracic impedance measurements along with ECG measurements to determine the patient's cardiac condition. Procedures for using impedance as a diagnostic marker, such as an indicator of the flow of blood in a patient, are known in the art.

Other non-invasive signals that may be used in accordance with the invention include phonocardiographic signals. The sounds of the patient's heart valves opening and closing, and the sounds of turbulent blood flow are indicative of perfusion in the patient, which is an aspect of cardiac condition useful for determining, for example, a non-shockable rhythm. Moreover, the timing characteristics of heart sounds detected in a patient are useful as indicators of peripheral resistance in the patient's circulatory system and load on the patient's heart.

Measures of blood oxygenation and pulsitile variation obtained using reflectance oximetry techniques may also be used to evaluate blood flow in a patient. As a whole, these measures and/or other measures such as patient temperature and blood pressure, along with the measures discussed above, may be used to determine a patient's cardiac condition. In that regard, one or more statistical classifiers, such as a classification and regression tree (as discussed in reference to FIGS. 5–13), is prepared using measures obtained from a population having a known cardiac condition. The classifier(s) is(are) later used to classify the same measures obtained from a patient under current evaluation. In accordance with the present invention, these measures are automatically evaluated to produce information for making decisions regarding triage and treatment.

The scope of the invention should therefore not be construed as limited to the specific embodiments discussed herein but be determined by the following claims and equivalents thereof The embodiments of the invention in which an exclusive property or privilege is claimed are defined as follows:

1. A method of evaluating ECG data to automatically detect and report cardiac asystole, comprising:
    (a) obtaining ECG data;
    (b) calculating one or more ECG measures from the ECG data;
    (c) classifying the ECG data in multiple classifiers using the one or more ECG measures, wherein each classifier in the multiple classifiers classifies the ECG data into a class indicative of cardiac condition, and wherein one class indicative of cardiac condition is indicative of cardiac asystole; and
    (d) reporting an asystole classification if the ECG data is classified in the class indicative of cardiac asystole.

2. The method of claim 1, wherein the one or more ECG measures includes a measure in the group consisting of average amplitude, average frequency, baseline content, R-wave count, and ECG rate.

3. The method of claim 1, wherein one of the multiple classifiers is a statistical binary classification and regression tree.

4. The method of claim 1, wherein a first classifier of the multiple classifiers classifies the ECG data into a rhythm class associated with a cardiac rhythm.

5. The method of claim 4, further comprising reporting the rhythm class into which the ECG data is classified.

6. The method of claim 4, wherein a second classifier of the multiple classifiers classifies the ECG data into a class associated with a shockable or non-shockable cardiac condition.

7. The method of claim 6, wherein the second classifier classifies the ECG data into a class associated with a shockable or non-shockable cardiac condition based on the rhythm class into which the first classifier classifies the ECG data.

8. The method of claim 6, further comprising setting a flag if the first classifier classifies the ECG data of a patient into a rhythm class indicative of cardiac perfusion, and if the second classifier classifies the ECG data of the patient into a class associated with a non-shockable cardiac condition, the flag indicating that on subsequent delivery of a defibrillation pulse to the patient, if the patient has previously received a defibrillation pulse, the subsequent defibrillation pulse should convey an amount of energy equal to the energy conveyed in the previous defibrillation pulse delivered most recently.

9. The method of claim 4, further comprising automatically prompting on a display a procedure to undertake based on the rhythm class into which the ECG data is classified.

10. The method of claim 9, wherein the procedure automatically prompted on the display is a therapy associated with the cardiac rhythm indicated by the rhythm class.

11. The method of claim 9, wherein the procedure is an instruction providing guidance for prioritizing the delivery of a therapy.

12. The method of claim 11, wherein the instruction includes providing CPR for a period of time followed by delivery of a defibrillation pulse if the rhythm class into which the ECG data is classified is associated with medium- to low-amplitude ventricular fibrillation, or providing immediate delivery of a defibrillation pulse if the rhythm class into which the ECG data is classified is associated with high-amplitude ventricular fibrillation.

13. The method of claim 9, further comprising grouping two or more rhythm classes to make a super class having an associated therapy, wherein the procedure automatically prompted on the display is a therapy based on the super class of the rhythm class into which the ECG data is classified.

14. The method of claim 1, wherein obtaining ECG data comprises obtaining a continuous stream of ECG data, and wherein classifying the ECG data is performed on the continuous stream of ECG data at one or more instances of time.

15. The method of claim 1, wherein obtaining ECG data comprises obtaining a segment of ECG data over an interval of time.

16. The method of claim 15, further comprising obtaining multiple segments of ECG data over different intervals of time and classifying each segment of the multiple segments of ECG data, wherein the step of reporting an asystole classification includes:
(a) determining an overall ECG classification based on the classification of each segment of the multiple segments of ECG data; and
(b) reporting the overall ECG classification if the overall ECG classification is indicative of cardiac asystole.

17. The method of claim 16, wherein the multiple segments of ECG data include three segments of ECG data, and the overall ECG classification is based on a consensus of the classification of two of the three segments.

18. The method of claim 1, further comprising recording the classification of the ECG data in a history of ECG classifications, and reporting an asystole classification only if the history of ECG classifications indicates that a predetermined number of ECG classifications over at least a predetermined period of time have resulted in an asystole classification.

19. The method of claim 1, wherein an asystole classification is not reported if a defibrillation pulse has been delivered within a predetermined period of time.

20. The method of claim 1, further comprising automatically charging one or more defibrillation capacitors to deliver a defibrillation pulse if the ECG data is classified in a class associated with a shockable cardiac condition.

21. The method of claim 1, further comprising obtaining additional signal data indicative of cardiac condition and calculating one or more signal measures from the additional signal data, the multiple classifiers using the one or more signal measures and the one or more ECG measures to classify the additional signal data and the ECG data into a class indicative of cardiac condition.

22. The method of claim 21, wherein the additional signal data is patient impedance data.

23. The method of claim 21, wherein the additional signal data is phonocardiographic data.

24. A method of evaluating ECG data to automatically detect and report cardiac asystole, comprising:
(a) obtaining ECG data;
(b) calculating one or more ECG measures from the ECG data;
(c) classifying the ECG data into a plurality of classes including shockable, asystole, and non-asystole classes using the one or more ECG measures;
(d) recording the classification of the ECG data in a history of ECG classifications; and
(e) reporting an asystole classification only if the history of ECG classifications indicates that a predetermined number of ECG classifications over at least a predetermined period of time resulted in an asystole classification.

25. The method of claim 24, wherein the one or more ECG measures includes a measure in the group consisting of average amplitude, average frequency, baseline content, R-wave count, and ECG rate.

26. The method of claim 24, wherein a statistical binary classification and regression tree is used to classify the ECG data.

27. The method of claim 24, wherein the ECG data are classified into a rhythm class associated with a cardiac rhythm, and wherein the ECG data are classified into one of the shockable, asystole, or non-asystole classes depending on the rhythm class into which the ECG data is classified.

28. The method of claim 27, further comprising reporting the rhythm class into which the ECG data is classified.

29. The method of claim 27, further comprising automatically prompting on a display a procedure to undertake based on the rhythm class into which the ECG data is classified.

30. The method of claim 29, wherein the procedure automatically prompted on the display is a therapy associated with the cardiac rhythm indicated by the rhythm class.

31. The method of claim 29, wherein the procedure is an instruction providing guidance for prioritizing the delivery of a therapy.

32. The method of claim 31, wherein the instruction includes providing CPR for a period of time followed by delivery of a defibrillation pulse if the rhythm class into which the ECG data is classified is associated with medium- to low-amplitude ventricular fibrillation, or providing immediate delivery of a defibrillation pulse if the rhythm class into which the ECG data is classified is associated with high-amplitude ventricular fibrillation.

33. The method of claim 24, wherein obtaining ECG data comprises obtaining a continuous stream of ECG data, and wherein classifying the ECG data is performed on the continuous stream of ECG data at one or more instances of time.

34. The method of claim 24, wherein obtaining ECG data includes obtaining multiple segments of ECG data over different intervals of time, wherein classifying the ECG data includes classifying each segment of the multiple segments of ECG data, and wherein reporting an asystole classification includes:
   (a) determining an overall ECG classification based on the classification of each segment of the multiple segments of ECG data; and
   (b) reporting the overall ECG classification if the overall ECG classification is indicative of cardiac asystole.

35. The method of claim 34, wherein the multiple segments of ECG data include three segments of ECG data, and the overall ECG classification is based on a consensus of the classification of two of the three segments.

36. The method of claim 24, wherein an asystole classification is not reported if a defibrillation pulse has been delivered within a predetermined period of time.

37. The method of claim 24, further comprising automatically charging one or more defibrillation capacitors to deliver a defibrillation pulse if the ECG data is classified in the shockable class.

38. The method of claim 24, further comprising obtaining additional signal data indicative of cardiac condition and using the one or more ECG measures and one or more signal measures calculated from the additional signal data to classify the additional signal data and the ECG data.

39. The method of claim 38, wherein the additional signal data is patient impedance data.

40. The method of claim 38, wherein the additional signal data is phonocardiographic data.

41. A medical device for automatically detecting and reporting cardiac asystole, comprising:
   (a) a plurality of electrodes configured to detect ECG signals;
   (b) a converter in signal communication with the plurality of electrodes for converting the ECG signals into ECG data;
   (c) a processing unit in signal communication with the converter for receiving and automatically evaluating the ECG data, the processing unit calculating one or more ECG measures from the ECG data and using the one or more ECG measures to classify the ECG data as shockable or non-shockable, and if classified as non-shockable, then classify the ECG data as asystole or non-asystole; and
   (d) a display in signal communication with the processing unit, the processing unit reporting a detection of asystole on the display if the ECG data is classified as asystole.

42. The medical device of claim 41, wherein the processing unit classifies the ECG data into a rhythm class associated with a cardiac rhythm, the processing unit further reporting the rhythm class into which the ECG data is classified and prompting a therapy on the display based on the rhythm class into which the ECG data is classified.

43. The medical device of claim 41, further comprising a memory in signal communication with the processing unit, wherein the memory stores a history of ECG classifications and the processing unit records the classification of the ECG data in the history of ECG classifications.

44. The medical device of claim 43, wherein the processing unit reports a detection of asystole only if the history of ECG classifications indicates that a predetermined number of ECG classifications over at least a predetermined period of time resulted in an asystole classification.

45. The medical device of claim 41, further including a defibrillation circuit in signal communication with the processing unit for delivering defibrillation pulses, wherein the processing unit does not report a detection of asystole if the defibrillation circuit has delivered a defibrillation pulse within a predetermined period of time.

46. The medical device of claim 45, wherein the defibrillation circuit includes one or more defibrillation capacitors and the processing unit automatically instructs the defibrillation circuit to charge the one or more defibrillation capacitors to deliver a defibrillation pulse if the processing unit classifies the ECG data as shockable.

47. The medical device of claim 45, wherein the medical device is an automated external defibrillator.

48. The medical device of claim 41, further comprising:
   (a) one or more sensors configured to detect a signal that is indicative of cardiac condition other than an ECG signal; and
   (b) a converter in signal communication with the one or more sensors for converting the signal indicative of cardiac condition into signal data;
   wherein the processing unit receives and evaluates the signal data with the ECG data, the processing unit calculating one or more signal measures from the signal data and using the one or more signal measures and the one or more ECG measures to classify the signal data and ECG data.

49. The medical device of claim 48, wherein the signal indicative of cardiac condition is an impedance signal.

50. The medical device of claim 48, wherein the signal indicative of cardiac condition is a phonocardiographic signal.

51. A medical device for automatically evaluating cardiac condition, comprising:
   (a) a plurality of sensors configured to detect one or more signals from a patient indicative of cardiac condition;
   (b) a converter in signal communication with the plurality of sensors for converting the one or more signals into signal data;
   (c) a processing unit in signal communication with the converter for receiving and automatically evaluating the signal data by classifying the signal data into a class indicative of cardiac condition, the processing unit determining an instruction based on the classification of the signal data for guiding a first-responding caregiver in providing emergency triage and treatment of the patient without the benefit of expert human intervention;
   (d) a memory in signal communication with the processing unit for receiving and recording the class into which the signal data is classified by the processing unit, the class being recorded in a history of ECG classifications in the memory; and
   (e) a display in signal communication with the processing unit, the processing unit prompting the instruction on the display, and if the history of ECG classifications stored in the memory indicates that a predetermined number of ECG classifications over at least a predetermined period of time resulted in an asystole classification, the processing unit also prompting notification of asystole on the display.

52. The medical device of claim 51, wherein the medical device is an automated external defibrillator and the one or more signals are ECG signals.

53. The medical device of claim 52, wherein the processing unit classifies the signal data into a rhythm class indicative of a cardiac rhythm, and wherein the instruction is tailored according to the cardiac rhythm of the rhythm class into which the signal data is classified.

54. The medical device of claim 53, wherein the processing unit uses a binary classification and regression tree to classify the signal data into a rhythm class.

55. The medical device of claim 52, further comprising one or more defibrillation capacitors, wherein the processing unit automatically charges the one or more defibrillation capacitors for delivery of a defibrillation pulse if the signal data is classified in a class indicative of a shockable cardiac condition.

56. The medical device of claim 51, wherein the processing unit automatically prompts an asystole detection on the display if the signal data is classified into a class indicative of cardiac asystole.

57. The medical device of claim 51, wherein the ECG classifications in the predetermined number of ECG classifications are consecutive ECG classifications.

58. The medical device of claim 57, wherein the predetermined period of time is at least four minutes.

59. The method of claim 18, wherein the ECG classifications in the predetermined number of ECG classifications are consecutive ECG classifications.

60. The method of claim 59, wherein the predetermined period of time is at least four minutes.

61. The method of claim 24, wherein the ECG classifications in the predetermined number of ECG classifications are consecutive ECG classifications.

62. The method of claim 61, wherein the predetermined period of time is at least four minutes.

63. The medical device of claim 44, wherein the ECG classifications in the predetermined number of ECG classifications are consecutive ECG classifications.

64. The medical device of claim 63, wherein the predetermined period of time is at least four minutes.

* * * * *

UNITED STATES PATENT AND TRADEMARK OFFICE
CERTIFICATE OF CORRECTION

PATENT NO. : 6,304,773 B1
DATED : October 16, 2001
INVENTOR(S) : J.W. Taylor et al.

It is certified that error appears in the above-identified patent and that said Letters Patent is hereby corrected as shown below:

<u>Column 25,</u>
Lines 20-25, delete in its entirety Claim 56

Signed and Sealed this

Twenty-third Day of April, 2002

Attest:

Attesting Officer

JAMES E. ROGAN
*Director of the United States Patent and Trademark Office*